US010687737B2

(12) United States Patent
Roskopf

(10) Patent No.: US 10,687,737 B2
(45) Date of Patent: Jun. 23, 2020

(54) METHODS, SYSTEMS AND KITS FOR ENHANCED MUSCLE CONTRACTILE CAPABILITIES

(71) Applicant: Greg Roskopf, Englewood, CO (US)

(72) Inventor: Greg Roskopf, Englewood, CO (US)

(73) Assignee: Muscle Activation Techniques, LLC, Englewood, CO (US)

( * ) Notice: Subject to any disclaimer, the term of this patent is extended or adjusted under 35 U.S.C. 154(b) by 557 days.

(21) Appl. No.: 15/065,665

(22) Filed: Mar. 9, 2016

(65) Prior Publication Data

US 2016/0262662 A1    Sep. 15, 2016

Related U.S. Application Data

(60) Provisional application No. 62/131,156, filed on Mar. 10, 2015.

(51) Int. Cl.
| A61B 5/11 | (2006.01) |
| A61B 5/00 | (2006.01) |
| A63B 23/00 | (2006.01) |
| A61H 99/00 | (2006.01) |
| A61H 1/02 | (2006.01) |

(52) U.S. Cl.
CPC .......... *A61B 5/1107* (2013.01); *A61B 5/1104* (2013.01); *A61B 5/4839* (2013.01); *A61B 5/4884* (2013.01); *A61B 5/4519* (2013.01); *A61H 1/02* (2013.01); *A61H 99/00* (2013.01); *A63B 23/00* (2013.01)

(58) Field of Classification Search
CPC .... A61B 5/1104; A61B 5/1107; A61B 5/4519
See application file for complete search history.

(56) References Cited

U.S. PATENT DOCUMENTS

| 5,434,142 A | 7/1995 | Antoku et al. |
| 2007/0106337 A1 | 5/2007 | Errico et al. |
| 2009/0280103 A1 | 11/2009 | Flueck |
| 2010/0004715 A1 | 1/2010 | Fahey |
| 2010/0174161 A1 | 7/2010 | Lynn |
| 2011/0112604 A1 | 5/2011 | Mushahwar et al. |
| 2012/0065629 A1 | 3/2012 | Elkins et al. |
| 2012/0133655 A1 | 5/2012 | Kristjansson |
| 2013/0165829 A1 | 6/2013 | Carroll |

FOREIGN PATENT DOCUMENTS

WO    2013177428 A1    11/2013

OTHER PUBLICATIONS

International Search Report for PCT/US2016/021607 and Written Opinion dated Aug. 8, 2016, 26 pages.

*Primary Examiner* — William H Matthews
(74) *Attorney, Agent, or Firm* — Brownstein Hyatt Farber Schreck, LLP

(57) ABSTRACT

Methods, systems and kits are disclosed for facilitating a subject's muscle contractile capabilities. Movement patterns with muscle hierarchy are also disclosed.

13 Claims, 1 Drawing Sheet

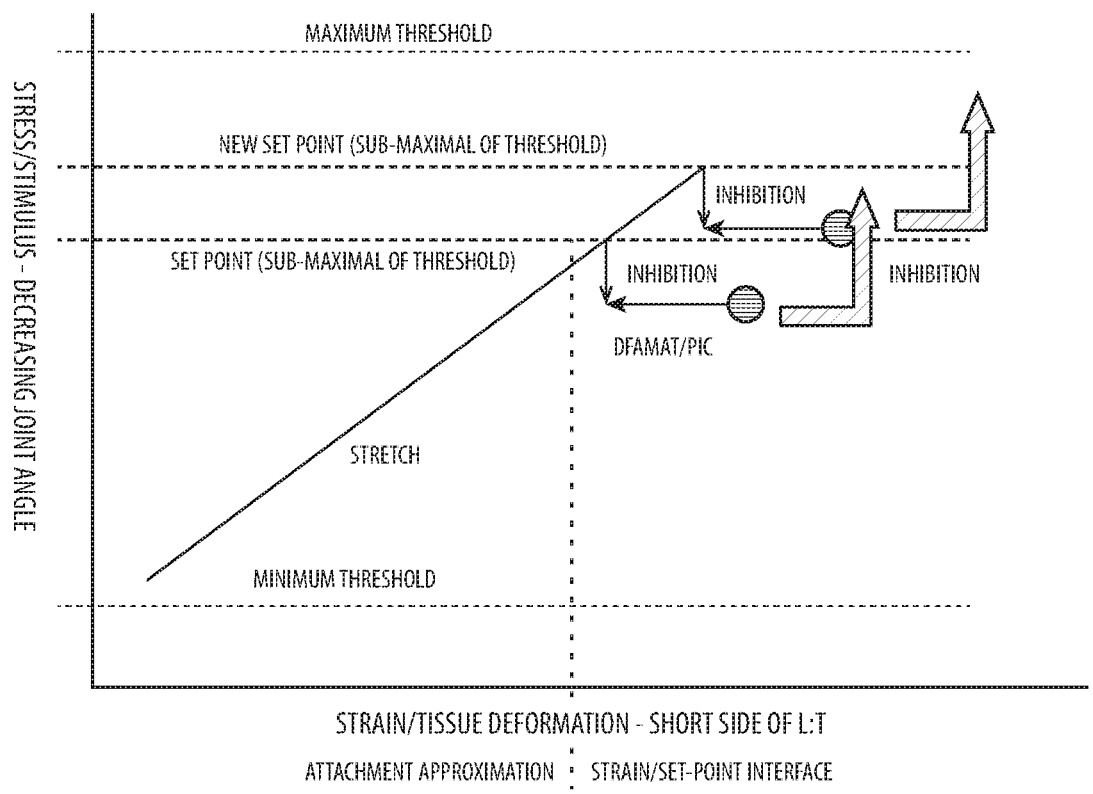

METHODS, SYSTEMS AND KITS FOR ENHANCED MUSCLE CONTRACTILE CAPABILITIES

RELATED APPLICATIONS

This application claims priority under 35 U.S.C. 119 (e) to U.S. Provisional Patent Application Ser. No. 62/131,156, entitled "Methods, Systems and Kits for Enhanced Muscle Contractile Capabilities," filed Mar. 10, 2015, the disclosure of which is hereby incorporated by reference in its entirety.

TECHNICAL FIELD

The disclosure generally relates to methods for maintaining and improving the contractile capability of one or more target muscles in a subject.

BACKGROUND OF THE INVENTION

Conventional muscle treatment is based on the diagnoses and treatment of muscle pain and weakness in hopes of limiting pain and improving an individual's ability to exercise and physically perform. Where pain is the issue, pain medications and anti-inflammatories are prescribed and in some cases injected into a problematic area. Conventional techniques also attempt to directly lengthen or change a muscle via stretching, heating, kneading and/or foam rolling a target muscle. These techniques are dictated by identification and treatment on the specific muscle or muscle location of the pain or weakness.

Techniques have also been developed on the principle that human movement and exercise is fundamental to health and that loss of muscle contractile efficiency may be demonstrated as a loss of motion and a decrease in physical performance. Identification and treatment of muscle pain and weakness is a persistent problem in need of additional solutions.

The present disclosure and embodiments described herein are directed toward providing novel solutions to improving and maintaining an individual's muscle contractile abilities.

The present invention is directed toward overcoming one or more of the problems discussed above.

BRIEF DESCRIPTION OF THE DRAWINGS

The described embodiments will be readily understood by the following detailed description in conjunction with the accompanying drawings.

FIG. 1 shows an illustration of raising the set-point via a strain/tissue deformation versus stress/stimulus graph.

SUMMARY OF THE INVENTION

Embodiments described herein provide methods, systems and kits for raising the tolerance and/or stability of one or more muscles in a subject. In some embodiments the method and systems are designed to enhance the contractile efficiency of some or all of a subject's muscles. Surprisingly, methods and systems described herein provide for a significant improvement over conventional therapeutic or exercise techniques.

Embodiments herein also include methods and systems for treating one or more target muscles in a subject based on administration of a treatment to the target muscle while that muscle is in an activated state.

The disclosure also provides kits for facilitating the effects of exercise on a problematic muscle or muscles in a subject in need thereof.

Embodiments herein characterize 43 primary movement patterns (herein "patterns") that account for movement in the human body. The classification of the 43 patterns is based on each pattern's function. Functional requirements of the 43 patterns are directed by the central and peripheral nervous systems. Each pattern includes a primary muscle and one or more secondary muscles.

DESCRIPTION

In more detail, stress application, using the methods, systems and kits described herein, initially causes a target muscle to exceed its current set-point level, thereby creating inhibition in that target muscle. Once inhibition has been achieved, the target muscle is ready for transition to an activated state, also referred to herein as the muscle being 'locked in.'

A stress can be re-applied to the target muscle after the muscle has been activated which will respond in the absence or with a lower state of inhibition to the applied stress. This process of stressing and treating a target muscle allows an increase in the target muscle's set-point towards the target muscles current maximum tolerance and stability level. The establishment of a new set point for the target muscle ultimately widens the physiological operating window of the target muscle. These methods, systems and kits described herein may be repeated over a period of time to incrementally increase a target muscle's set point (see FIG. 1). As referred to herein, a widening of the physiological operating window of a target muscle means that the muscle has increase contractile efficiency and has an improved ability to tolerate greater amounts of force. As a target muscle is stressed and treated that target muscle enters a "locked-in state" where the cycle of treatment becomes more effective than for a similarly treated muscle not in a "locked in" state.

In addition and surprisingly, where alternative treatment, beyond treatment to increase a muscle's set point is necessitated, for example, where a target muscle is in need of repair due to pain, tears, sprains, loss, strain, aches, etc., the alternative treatment is greatly facilitated by application when the target muscle is in a "locked in" state. For example, facilitating the utility of a biologic in a target muscle is facilitated by implanting the biologic into the target muscle in order to activate that muscle pattern by the methods, systems and kits of the present invention. For purposes herein a biologic agent or biologic is any substance used in the prevention or treatment of a muscle pain, injury or disease state. Illustrative biologic agents include: autologous and non-autologous stem cells, anti-inflammatories including anti-rheumatic drugs, immunosuppressants like Methotrexate and azathioprine, anti-cytokines to reduce inflammation like anti-Tumor Necrosis Factor (anti-TNF), medications to repair muscle damage like steroids, platelet-rich plasma or bone-marrow aspirate, chemotherapeutics for treatment of cancer residing in the muscle, for example Alemtuzumab, and the like.

Methods for Activating a Target Muscle:

Generally, methods disclosed herein provide for the application of stress, and thereby treatment, in a pre-determined priority based on the hierarchy of muscles between each pattern, i.e., a muscle's macro-pattern. In addition, this hierarchy of muscles extends within the patterns themselves thereby establishing a micro-pattern wherein each muscle within a pattern has a hierarchy including one primary muscle and one or more secondary muscles. The patterns are ordered bilaterally from left to right (left first, then right).

Embodiments herein provide that each of the identified 43 movement patterns have one primary muscle (a subject has 43 primary muscles) and a corresponding number of secondary muscles. As such, the hierarchy between a subject's muscles described herein can be described between muscle patterns, between primary muscles, as well as within a pattern itself (one primary and a number of secondary muscles). A macro-pattern is the overall hierarchy between all 43 movement patterns, and a micro-pattern is the hierarchy between muscles within any one muscle pattern.

The hierarchy of muscles within the human body provides a unexpected window from and during which one or more of a subject's muscles, within a pattern, is more effectively treated to either enhance that muscle groups set point or provide alternative treatments meant to facilitate healing of an injury to that muscle. The hierarchy can also be utilized to methodically enhance the set point of individual patterns including some or all of a subject's muscles and thereby facilitate the subject's musculature in general or facilitate maintenance of a subject's musculature against aging and health defects.

As such, each macro- and micro-pattern has been mapped herein to identify the order within which each muscle is first placed under stress or is tested and then, after weakness is identified, treated. In this manner each muscle within the body, targeted or not, can be treated in a way to maximize the effectiveness of the treatment.

In some embodiments the hierarchy established and mapped in the present disclosure is between two or more patterns, i.e., between any two or more primary muscles. The hierarchy provides a stress and treatment hierarchy for any two, three, four, five, six, seven, . . . forty one, forty two, forty three primary muscles in the absence of a pattern's secondary muscles. As such, priority is mapped to start the process at a first primary muscle and extend through the macro-pattern of all the primary muscles (43). Testing and treatment of a subject's macro-pattern then includes bilaterally challenging each pattern via stress application (L then R), a prioritized primary muscle to identify a bilateral weakness. When a primary muscle requires treatment (see below) the treatment is applied. Regardless, once bilateral testing and treatment (if necessary) is concluded on the first or most prioritized primary muscle the health care professional moves onto the next highest prioritized muscle group, testing for bilateral weakness. This process holds true for the hierarchy of the 43 primary muscles (see Table 1). In some embodiments all 43 primary muscles are tested and treated in the order as disclosed in Table 1, from 1-43. In other embodiments, a primary muscle is tested and treated in an order where the primary muscle having a lower group number is always tested and treated prior to a next primary muscle, for example from 1, 7, to 9. In this way a health care professional may wish to treat a primary muscle of group 22 and deem it appropriate to start the process at the primary muscle of group 3, then 4-9, then 15-22, for example. At no time would the process start with a priority number higher than the target group primary number, e.g., 27, 25 then 22, for example. However, a health care professional may deem it necessary or advantageous to continue treatment beyond the target number, for example continue on from 22 to treat 27-31 and 40-43 (in order). In some instances where the subject has been treated via the methods described herein or is an elite athlete, fewer primary muscles may need to be tested and treated. It is also envisioned that the health care professional start the process and move bilaterally from group 1 to group 22 (in this example).

In another embodiment, priority is mapped to start the bilateral process at a first muscle in the first muscle group, i.e., the group's left primary muscle, and extend through that group's secondary muscle hierarchy, the micro-pattern. In some embodiments, the process is then continued to the first muscle, primary muscle, in the next prioritized pattern. Embodiments herein include establishing the hierarchy between two or more of the 43 patterns, three or more of the 43 total patterns, four or more of the 43 total patterns (4/43) and so on (5/43), (6/43), (7/43), (8/43), (9/43), (10/43) . . . (42/43), (43/43). In this way, the hierarchy has been identified for and between all 43 patterns (primary and secondary muscles) providing a pattern that establishes enhanced treatment for all muscles within all 43 patterns. In some subjects, the application of a specific stress (MSAS), muscle weakness identification and treatment (AMC&S) is performed on all muscles within all 43 patterns in the disclosed herein hierarchy. However, any combination can be achieved as long as the processes herein follow the hierarchy established and described herein, i.e., started with a pattern's primary muscle and, where appropriate, that pattern's secondary muscles, in a pattern prioritized above the next to be treated pattern's primary, and where appropriate, secondary muscles. As noted for the macro-pattern, the micro-patterns are established bilaterally. So, the hierarchy begins with the left primary muscle and moves to the pattern's right primary muscle, then to the left highest priority left muscle and so on.

As such, a first muscle (left, primary) in a pattern having the highest priority of the 43 patterns (referred to herein as pattern 1) has been identified all the way through to the last muscle (a right, secondary muscle) in the lowest priority pattern (referred to herein as muscle pattern 43). Typically and unexpectedly maximum benefit is achieved for any one muscle group when stress or testing is applied to the associated muscles within the macro- and micro-patterns of patterns and more beneficially when stress or testing is applied to the muscle group after the muscles in one or more higher priority pattern is first stressed according to embodiments of the present disclosure. Further, the criteria of maximum benefit for a muscle group is achieved when stress and testing is applied to the muscle in the heretical order of two or more higher priority patterns prior to the muscle pattern within which the target muscle resides, more beneficially three or more patterns, etc. until all of the muscles within all of the higher priority patterns have been activated or locked-in. So for example, if a secondary muscle in pattern 7 is the target muscle (e.g., injured), the muscles within the first 6 patterns and then within pattern 7 would first be stressed or tested prior to activation (bilaterally).

Note also that the disclosure herein also contemplates a process where, using the example above, the first 6 pattern's primary and secondary muscles are treated in order, bilaterally, followed by the 7 group's primary muscle and then hierarchy of secondary muscles within pattern 7, in order, including the target muscle.

Stress application in accordance with the present disclosure is established for each pattern based on the muscle pattern's primary function. In general, and in one embodiment, stress application to a muscle is accomplished by a Muscle Specific Applied Stress (MSAS) (Table 2). Other like specific stress methodologies can be utilized herein. MSAS is applied by a health care professional. A health care professional for purposes herein refers to licensed and non-licensed providers and includes: medical doctors, doctors of osteopathy, doctors of chiropractic, doctors of physical therapy, massage therapists, nurses, trainers, strength and conditioning coaches and the like.

The inventor's philosophy recognizes that passive range of motion limitations correlate with muscle weaknesses. The inventor also recognizes that the assessment of passive range of motion can expose inhibition. So, if an inhibited muscle cannot contract efficiently, then it cannot effectively shorten. This is also demonstrated by the opposite muscles inability to effectively lengthen. Many times, even though there are limitations in range of motion, the muscles associated with that loss of range of motion will still test strong when performing the AMC&S test. This is a representation that the set point has not been exceeded, but the limitation in motion is still a representation of vulnerability or potential weakness.

MSAS is a passive stress that is applied in a controlled environment that is designed to expose these potential vulnerabilities. MSAS shortens target muscle's that relate to the limitation in the range of motion. It is evidenced that by passively shortening a target muscle that has a lower set point, the opposite muscle(s) which display increased tension will be lengthened. This passive stretch, takes the joint into a range of motion that the body has been avoiding. In doing so, the passive stretch exposes muscle weaknesses that may not have shown up previously through the AMC&S testing. Each of the 43 patterns has a specific MSAS that is specific to the function of the associated primary and secondary muscles in that pattern (see Table 2). Therefore, if a limitation in ROM exists that is specific to the function of 1 of the 43 patterns, those weaknesses can be exposed through the application of that patterns MSAS. This provides an environment where those muscles can be treated and the associated set point can be raised. By repeating the MSAS, like a vaccination, the set point can be continually raised until the point that the associated muscles no longer go weak in response to the MSAS (see FIG. 1).

A MSAS must be applied in a consistent and specific manner for each muscle group. Note that applied stress in accordance with MSAS should not lock the body in to a less specific stress as this will actually lower the target muscle's stress point. Further, application of MSAS pursuant to embodiments herein should not be changed midstream as this will provide for a decrease in a muscle's set point and finally the health care professional should always consider all the muscles in the muscle pattern (micro-pattern) and should show as weak relative to the non-specific stress(es).

In order to determine whether a muscle is showing weakness based on MSAS, several assessment techniques can be used. In one embodiment, Active Muscle Contract and Sustain Test (AMC&S) is utilized to identify a target muscle's weakness.

Typically a AMC&S is a muscle testing technique that is specific to embodiments described herein. AMC&S involves a specific force application of a specific magnitude and rate of force application, set-up and delivered by a health care specialist (see Example 2). The health care specialist assesses the target muscle's ability to react to and meet that force. AMC&S is not a manual muscle "break" test or manual muscle test used as an indication of the body's response to a chemical substance, nor a change in its energetic field, nor a positional post isometric relaxation technique.

In accordance with the present disclosure, AMC&S are initiated by the health care practitioner placing the subject in the proper testing position. The subject must relax and then hold the muscle against an applied stress with maximal effort. The health care practitioner takes care not to force the target muscle in multiple directions and should only use passive motion in the plane that matches the applied testing force (for example, adduction on posterior tibialis). It is also important that the subject utilize unconscious control as much as possible and avoid consciously interfering with the muscle's reaction to the applied stress through compensatory motion. Note that the subject's testing position is dictated by his or hers available ROM, therefore the testing positions will be different with each subject. This may require the health care professional to challenge all testing positions in a pattern (Example 2).

In a second embodiment herein, prior to the assessment a Passive Comparative Assessment of Mobility (CAM) is performed. CAM is a range of motion assessment that is specific to embodiments disclosed herein. CAM is a specific force application leading to the measurement of active or passive limb motion from a designated start position/posture, through a designated plane and direction, to the end of the limb motion. The measurement is then compared to the mirror image limb motion for the limb on the opposite side of the body. CAM is not a joint range of motion examination performed to evaluate passive tissue stability, joint surface pathology, ligamentous integrity, etc. CAM is typically used on a first visit to a health care professional prior to the AMC&S. However, CAM is optional for all other embodiments as described herein.

Once a muscle is shown to be properly stressed and in need of treatment, embodiments herein contemplate use of Digital Force Application To Muscle Attachment Technique (DFAMAT) or Positional Isoangular Contraction (PIC) technique (Table 3).

Typically a treatment in PIC is an activation technique specific to embodiments described herein. PIC involves a specific limb position/orientation (based on the macro and micro patterns shown and discussed herein) and direction of motion generated by the subject, into a barrier to that motion, set-up and maintained by a health care specialist. The health care specialist may use their hands and body to hold/guide limb orientation/positions and provide the barriers to motion during the isoangular contraction. PIC is not a muscle energy technique, strain/counter-strain technique or a post isometric relation technique.

Typically a treatment through DFAMAT is also an activation technique specific to embodiments described herein. DFAMAT involves a specific force application to a target muscle using the health care professional's fingers. The health care professional applies direct pressure perpendicular to a target muscle's attachment (tendons, aponeuroses) using the tips of the fingers instituting motion creating subtle tension on the attachment tissues, followed with motion lines that are perpendicular to each other, maintaining the tension for a duration of 1 to 4 seconds per site, and more typically 1 to 2 seconds per site, releasing and then re-initiating the process, moving along the width/length of the target muscle attachment. DFAMAT is not a soft tissue evaluation nor a manipulation to release trigger points, adhesions, Active Release Technique, move body fluids to and from tissue sites, etc.

Note that DFAMAT is not used to evaluate and interpret the state of soft tissues, nor to create a relaxation response for the target muscle. The premise of DFAMAT is that it stimulates sensory receptors that in turn increase motor neuronal pool activation to the target muscle associated with the attachment. This represents the opposite effect that most, if not all, massage techniques are attempting to achieve as an outcome (relaxation).

In accordance with the present disclosure and DFAMAT, a treatment is applied to the target muscle via palpation to the relevant bone where the target muscle is attached. Identification of the target muscle attachment point requires specific palpation such that as micro-pattern of muscles is being tested the then re-tested. Other treatment procedures for increasing a target muscle's set point include isometric and isotonic contractions and the like. Treatments may also include the injection (e.g. intramuscular, intradermal, intravenous) or ingestion of an appropriate biologic.

Biologics contemplated for use herein on an activated or locked-in muscle include: autologous and non-autologous stem cells, anti-inflammatories including anti-rheumatic drugs, immunosuppressants like Methotrexate and azathioprine, anti-cytokines to reduce inflammation like anti-Tumor Necrosis Factor (anti-TNF), medications to repair muscle damage like steroids, platelet-rich plasma or bone-marrow aspirate, chemotherapeutics for treatment of cancer residing in the muscle, for example melanoma (Alemtuzumab, for example), and the like.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

Example 1

Movement Pattern Hierarchy and Tables 2-3 Showing Illustrative Tests

The following hierarchy has been established for the 43 movement patterns as classified for purposes herein. This hierarchy from pattern 1 to 43 represents the macro-pattern:

TABLE 1

(Movement Patterns, Left then Right)

| Group/Pattern Number | Muscle Pattern Macro-Order | Primary Muscle |
|---|---|---|
| 1 | Trunk Rotation | Transverse Abdominis - Lower Division |
| 2 | Trunk Flexion | Psoas Minor |
| 3 | Hip Flexion | Psoas Major: Lumbar Division |
| 4 | Hip Rotation | Obturator Externus |
| 5 | Spinal Sidebend | Longissimus Thoracis |
| 6 | Downward Rotation of the Scapula | Levator Scapula: Superior Division |
| 7 | Humeral External Rotation | Infraspinatus: Superior Division |
| 8 | Spinal Extension | Intertransversatii: Lumborum |
| 9 | Hip Extension | Gluteus Maximus: Iliac Division |
| 10 | Humeral Extension and Adduction | Latissimus Dorsi: Iliac Division |
| 11 | Humeral Internal Rotation | Subscapularis: Superior Division |
| 12 | Elbow Extension | Triceps Brachii: Medial Division |
| 13 | Upward Rotation of the Scapula | Upper Trapezius: Clavicular Division |
| 14 | Humeral Abduction | Supraspinatus: Fossa Division |
| 15 | Protraction of the Scapula | Pectoralis Minor: Inferior Division |
| 16 | Horizontal Adduction | Pectoralis Major: Sternal Division |
| 17 | Elbow Flexion | Brachialis |
| 18 | Hip Adduction | Adductor Magnus: Oblique Division |
| 19 | Hip Abduction | Gluteus Medius: Anterior Division |
| 20 | Knee Extension | Rectus Femoris: Straight Division |
| 21 | Knee Flexion | Semitendinosus |
| 22 | Supination of the Foot | Posterior Tibialis: Fibular Division |
| 23 | Plantarflexion | Medial Soleus |
| 24 | $1^{st}$ Ray Dorsiflexion | Anterior Tibialis: Tibial Division |
| 25 | Pronation | Peroneus Brevis: Lateral Division |
| 26 | Dorsiflexion | Peroneus Tertius: Lateral Division |
| 27 | $1^{st}$ Ray Plantarflexion | Peroneus Longus: Metatarsal Division |
| 28 | Big Toe Extension | Extensor Hallucis Longus: Fibular Division |
| 29 | Toe Extension | Extensor Digitorum Longus: Lateral Division |
| 30 | Big Toe Flexion | Flexor Hallucis Longus: Fibular Division |
| 31 | Toe Flexion | Flexor Digitorum Longus: Lateral Division |
| 32 | Cervical Flexion | Longus Capitis |
| 33 | Cervical Rotation | Multifidus Cervicis: Inferior Fibers |
| 34 | Cervical Extension | Semispinalis Capitis |
| 35 | Cervical Sidebend | Posterior Scalene |
| 36 | Wrist Extension with Abduction | Extensor Carpi Radialis Longus: Abductor Division |
| 37 | Wrist Flexion with Abduction | Flexor Carpi Radialis Longus: Abductor Division |
| 38 | Forearm Supination | Anconeus: Ulnar Division |
| 39 | Forearm Pronation | Pronator Teres: Humeral Division |
| 40 | Extension and Abduction of the Thumb | Extensor Pollicis Longus: Ulnar Division |
| 41 | Flexion and Abduction of the Thumb | Flexor Pollicis Longus |
| 42 | Finger Extension | Extensor Digitorum: Medial Division |
| 43 | Finger Flexion | Flexor Digitorum Profundus: Medial Division |

Hierarchy within a Movement Pattern (Micro-Pattern) (Bi-lateral, Left First and then Right):

Pattern 1 (Trunk Rotation):
Transverse Abdominis—Lower Division
Internal Oblique: Anterior Division
External Olique: Anterior Division
Semispinalis Thoracis
Transverse Abdominis: Upper Division
Sternalis
$4^{th}$ Rectus: Lateral Division
$4^{th}$ Rectus: Medial Division
Pattern 2 (Trunk Flexion):
Psoas Minor
Pyramidalis
$1^{st}$ Rectus Abdominis
$2^{nd}$ Rectus Abdominis
$3^{rd}$ Rectus Abdominis
Pattern 3 (Hip Flexion)
Psoas Major: Lumbar Division
Psoas Major: Thoracic Division
Psoas Major: Diaphragmatic Division
Iliacus Major
Iliacus Minor
Tensor Fascia Latae: Posterior Division
Tensor Fascia Latae: Anterior Division
Pattern 4 (Hip Rotation)
Obturator Externus
Quadratus Femoris
Piriformis
Gemellus Inferior
Gemellus Superior
Adductor Minimus
Obturator Internus
Pattern 5 (Spinal Sidebend)
Longissimus Thoracis
Longissimus Lumborum
Internal Obliques: Lateral Division
External Obliques: Lateral Division
Iliocostalis Thoracis
Iliocostalis Lumborum
Multifidus Thoracis
Multifidus Lumborum
Quadratus Lumborum: Spinal Division
Serratus Posterior: Inferior Division
Serratus Posterior: Superior Division
Quadratus Lumborum: Costal Division
Pattern 6 (Downward Rotation of the Scapula)
Levator Scapula: Superior Division
Levator Scapula: Inferior Division
Rhomboid Minor
Rhomboid Major
Pattern 7 (Humeral External Rotation)
Infraspinatus: Superior Division
Infraspinatus: Superior-Middle Division
Infraspinatus: Inferior-Middle Division
Infraspinatus: Inferior Division
Teres Minor
Pattern 8 (Spinal Extension)
Intertransversarii Lumborum
Interspinalis Lumborum
Spinalis Thoracis
Spinalis Lumborum
Rotatores Thoracis
Rotatores Lumborum
Pattern 9 (Hip Extension)
Gluteus Maximus: Iliac Division
Gluteus Maximus: Sacral Division
Gluteus Maximus: Coccygeal Division
Pattern 10 (Humeral Extension and Adduction)
Latissimus Dorsi: Iliac Division
Latissimus Dorsi: Lumbar Division
Latissimus Dorsi: Thoracic Division
Teres Major: Inferior Division
Teres Major: Superior Division
Tricep Brachii: Long Head
Pattern 11 (Humeral Internal Rotation)
Subscapularis: Superior Division
Subscapularis: Superior/Middle Division
Subscapularis: Inferior/Middle Division
Subscapularis: Inferior Division
Pattern 12 (Elbow Extension)
Triceps Brachii: Medial Division
Triceps Brachii: Lateral Division
Articularis Cubiti
Pattern 13 (Upward Rotation of the Scapula)
Upper Trapezius: Clavicular Division
Upper Trapezius: Scapular Division
Middle Trapezius
Lower Trapezius
Serratus Anterior: Superior Division
Serratus Anterior: Inferior Division
Subclavius: Lateral Division
Subclavius: Medial Division
Pattern 14 (Humeral Abduction)
Supraspinatus: Fossa Division
Supraspinatus: Spinal Division
Posterior Deltoid: Medial Division
Posterior Deltoid: Lateral Division
Middle Deltoid: Posterior Division
Middle Deltoid: Anterior Division
Anterior Deltoid: Acromial Division
Anterior Deltoid: Clavicular Division
Pattern 15 (Protraction of the Scapula)
Pectoralis Minor: Inferior Division
Pectoralis Minor: Superior Division
Pattern 16 (Horizontal Adduction)
Pectoralis Major: Sternal Division
Pectoralis Major: Clavicular Division
Pectoralis Major: Costal Division
Bicep Brachii: Long Head
Bicep Brachii: Short Head
Coracobrachialis: Inferior Division
Coracobrachialis: Superior Division
Pattern 17 (Elbow Flexion)
Brachialis
Brachioradialis: Superior Division
Brachioradialis: Inferior Division
Pattern 18 (Hip Adduction)
Adductor Magnus: Oblique Division
Adductor Magnus: Vertical Division
Adductor Longus: Superior Division
Adductor Longus: Inferior Division
Adductor Brevis
Pectineus
Gracilis
Pattern 19 (Hip Abduction)
Gluteus Medius: Anterior Division
Gluteus Medius: Posterior Division
Gluteus Medius: Anterior Division
Gluteus Minimus: Anterior Division
Gluteus Minimus: Posterior Division
Pattern 20 (Knee Extension)
Rectus Femoris: Straight Division
Rectus Femoris: Reflected Division Vastus Intermedius: Medial Division
Vastus Intermedius: Lateral Division
Vastus Medialis: Superior Division
Vastus Medialis: Middle Division
Vastus Medialis: Inferior Division
Vastus Lateralis: Superior Division
Vastus Lateralis: Middle Division
Vastus Lateralis: Inferior Division
Articularis Genu
Pattern 21 (Knee Flexion)
Semitendinosus
Semimembranosus: Lateral Division
Semimembranosus: Medial Division
Biceps Femoris: Short Head
Biceps Femoris Long Head: Fibular Division
Biceps Femoris Long Head: Tibial Division
Sartorius
Popliteus
Pattern 22 (Supination)
Posterior Tibialis: Fibular Division
Posterior Tibialis: Tibial Division
Pattern 23 (Plantarflexion)
Medial Soleus
Lateral Soleus
Lateral Gastroc
Medial Gastroc
Plantaris
Pattern 24 ($1^{st}$ Ray Dorsiflexion)
Anterior Tibialis: Tibial Division
Anterior Tibialis: Interossei Division
Pattern 25 (Pronation)
Peroneus Brevis: Lateral Division
Peroneus Brevis: Posterior Division
Pattern 26 (Dorsiflexion)
Peroneus Tertius: Lateral Division
Peroneus Tertius: Anterior Division
Pattern 27 ($1^{st}$ Ray Plantarflexion)
Peroneus Longus: Metatarsal Division
Peroneus Longus: 1st Cuneiform Division
Pattern 28 (Big Toe Extension)
Extensor Hallucis Longus: Fibular Division
Extensor Hallucis Longus: Interoseii Division
Extensor Hallucis Brevis
Pattern 29 (Toe Extension)
Extensor Digitorum Longus: Lateral Division
Extensor Digitorum Longus: Medial Division
Extensor Digitorum Brevis
Dorsal Interoseii 2-5
Pattern 30 (Big Toe Flexion)
Flexor Hallucis Longus: Fibular Division
Flexor Hallucis Longus: Interosseii Division
Flexor Hallucis Brevis: $1^{st}$ Cuneiform Division
Flexor Hallucis Brevis: Cuboid Division
Flexor Hallucis Brevis: $3^{rd}$ Cuneiform/Tensonal Division
Adductor Hallucis Longus: Oblique Head
Adductor Hallucis Longus: Transverse Head, Lateral
Adductor Hallucis Longus: Transverse Head, Medial
Abductor Hallucis Longus: Invertor Division
Abductor Hallucis Longus: Adductor Division
Pattern 31 (Toe Flexion)
Flexor Digitorum Longus: Lateral Division
Flexor Digitorum Longus: Medial Division
Flexor Digitorum Brevis: Lateral Division
Flexor Digitorum Brevis: Medial Division
Quadratus Plantae: Lateral Division
Quadratus Plantae: Medial Division
Lumbricals: 5-2
Plantar Interoseii: 5-3
Abductor Digiti Minimi
Flexor Digiti Minimi Brevis
Pattern 32 (Cervical Flexion)
Longus Capitis
Longus Colli: Superior Oblique Fibers
Longus Colli: Vertical Fibers
Longus Colli: Inferior Fibers
Mylohyoid
Sternohyoid
Rectus Capitis Anterior
Pattern 33 (Cervical Rotation)
Multifidus Cervicis: Interior Fibers
Multifidus Cervicis: Superior Fibers
Sterno-cleadomastoid: Sternal Fibers
Sterno-cleadomastoid: Clavicular Fibers
Longissimus Capitis
Longissimus Cervicis
Splenius Capitis: Occipital Fibers
Splenius Capitis: Mastoid Fibers
Splenius Cervicis
Iliocostalis Cervicis
Rotatores Cervicis
Rectus Capitis Posterior Major
Obliques Capitis Inferior
Pattern 34 (Cervical Extension)
Semispinalis Capitis
Semispinalis Cervicis
Spinalis Capitis
Spinalis Cervicis
Interspinalis Cervicis
Obliques Capitis Superior
Rectus Capitis Posterior Minor
Pattern 35 (Cervical Sidebend)
Posterior Scalene
Middle Scalene
Anterior Scalene
Anterior Intertransversarii
Posterior Intertransversarii
Omohyoid
Rectus Capitis Lateralis
Pattern 36 (Wrist Extension with Abduction)
Extensor Carpi Radialis Longus: Abductor Division
Extensor Carpi Radialis Longus: Extensor Division
Extensor Carpi Ulnaris Longus: Adductor Division
Extensor Carpi Ulnaris Longus: Extensor Division
Extensor Carpi Radialis Brevis
Pattern 37 (Wrist Flexion with Abduction)
Flexor Carpi Radialis Longus: Abductor Division
Flexor Carpi Radialis Longus: Flexor Division
Flexor Carpi Ulnaris Longus: Adductor Division
Flexor Carpi Ulnaris Longus: Flexor Division
Palmaris Longus
Pattern 38 (Forearm Supination)
Anconeus: Ulnar Division
Anconeus: Olecranon Division
Supinator: Olecranon Division
Supinator: Ulnar Division
Pattern 39 (Forearm Pronation)
Pronator Teres: Humeral Division
Pronator Teres: Ulnar Division
Pronator Quadratus: Proximal Division
Pronator Quadratus: Distal Division
Pattern 40 (Extension and Abduction of the Thumb)
Extensor Pollicis Longus: Ulnar Division
Extensor Pollicis Longus: Septal Division
Extensor Pollicis Brevis: Radial Division Extensor Pollicis Brevis: Septal Division
Abductor Pollicis Longus: Radial Division
Abductor Pollicis Longus: Ulnar Division
Pattern 41 (Flexion and Abduction of the Thumb)
Flexor Pollicis Longus
Abductor Pollicis Brevis
Flexor Pollicis Brevis
Adductor Pollicis: Oblique Head
Adductor Pollicis: Transverse Head
Interosseus Pollicis
Opponens Pollicis: Flexor Division
Opponens Pollicis: Abductor Division
Pattern 42 (Finger Extension)
Extensor Digitorum: Medial Division
Extensor Digitorum: Lateral Division
Extensor Indicis
Extensor Digiti Minimi
Dorsal Interoseii: 1-4
Pattern 43 (Finger Flexion)
Flexor Digitorum Profundus: Medial Division
Flexor Digitorum Profundus: Lateral Division
Flexor Digitorum Superficialis: Medial Division
Flexor Digitorum Superficialis: Lateral Division
Lumbricals: 4-1
Palmar Interoseii: 4-2
Flexor Digiti Minimi
Abductor Digiti Minimi: Flexor Division
Abductor Digiti Minimi: Abductor Division
Oponens Digiti Minimi Manus: Flexor Division
Oponens Digiti Minimi Manus: Abductor Division
Palmaris Brevis

TABLE 2

MSAS - Passive Shortening

| MSAS (Pattern Number) | Tester Position | Subject Position | Applied Force and/or Desired Stress |
|---|---|---|---|
| 1. Transverse Abdominis: Lower Division | Body: Stand on uninvolved side<br>Stabilizing Hand: posterior-lateral side of involved ilium to hold end range spinal rotation<br>Action Hand: contact on medial side of involved knee **maintain endrange rotation | Supine, Anchor thorax by wrapping arms around top of table<br>Head in headpiece<br>Flex hip to 90 degrees, with knee slightly flexed.<br>Adduct thigh in order to create spinal rotation | Desired Stress:<br>End range trunk rotation |
| 2. Psoas Minor | Body: Stand on involved side*<br>Guiding Hand: posterior side of involved shoulder<br>Action Hand: stabilize across back guiding thorax into end range of trunk and spinal flexion | Supine, with feet on the table and knees slightly bent<br>Feet shoulder width apart<br>Fully flex trunk and spine<br>Reach forward toward associated foot/feet | Desired Stress:<br>End range trunk flexion (each direction) |
| 3. Psoas Major | Body: Stand on involved side<br>Leg across uninvolved thigh<br>Stabilizing Hand: Brace involved thigh<br>Action Hand: grab lower leg at ankle | Supine, Anchor thorax by wrapping arms around top of table<br>Fully flex hip with knee extension | Desired Stress:<br>End range Hip flexion |
| 4. Hip External Rotation | Body: stand on involved side<br>Leg across opposite thigh<br>Stabilizing Hand: lateral side of involved knee<br>Action Hand: cup involved heel | Supine, Anchor thorax by wrapping arms around top of table<br>Flex involved hip<br>Fully externally rotate the femur at the hip with just below parallel to the table | Desired Stress:<br>End Range Hip External Rotation |
| 5. Spinal Sidebend | Body: Stand on involved side<br>Stabilizing Hand: stabilize uninvolved thorax in to inferior rib cage<br>Action Hand: reach arm under knees, grabbing inferior-lateral side of uninvolved knee at fibula<br>Take both legs to involved side to create spinal sidebend | Supine, slide body to the top of the uninvolved side of the table<br>Anchor uninvolved side arm around upper corner of table<br>Sidebend thorax on ilium<br>Grab side of table with involved hand | Desired Stress:<br>End Range Trunk Sidebend |
| 6. Downward Rotation | Body: Stand on involved side<br>Stabilizing Hand: inferior angle of scapula<br>Action Hand: Superior to AC joint | Prone, head in headrest<br>Rotate head to involved side<br>Arm to side of the body | Applied Force:<br>Elevate inferior angle of the scapula with stabilizing hand<br>Downwardly rotate the scapula through the acromion while maintaining position of the inferior angle |

TABLE 2-continued

MSAS - Passive Shortening

| MSAS (Pattern Number) | Tester Position | Subject Position | Applied Force and/or Desired Stress |
|---|---|---|---|
| | | | Desired Stress: End Range Downward Rotation of the scapula |
| 7. Humeral External Rotation | Body: Stand on involved side<br>Stabilizing Hand: posterior-lateral side of involved shoulder**<br>Action Hand: Around involved wrist<br>Brace involved elbow on thigh* | Supine, slide to edge of the table<br>Flex elbow 90 degrees<br>Abduct humerus 120 degrees<br>Fully externally rotate humerus | Desired Stress: End Range Humeral External Rotation |
| 8. Spinal Extension | Body: Stand at end of table, distal to client<br>Grab anterior aspect of both arms to assist in extension and opposite rotation<br>Maintain end range extension and rotation by holding uninvolved side arm/shoulder up and back | Prone, head in headset<br>Hands behind head<br>Fully extend and rotate thorax to opposite side | Desired Stress: End Range Spinal Extension |
| 9. Hip Extension | Body: stand on involved side<br>Stabilizing hand: posterior, superior pelvis and sacrum on involved side<br>Action hand: anterior, Lower ⅓rd of involved thigh | Prone, 90 degrees of knee flexion<br>Slight abduction of involved thigh*<br>Fully extend hip | Desired Stress: End Range Hip Extension |
| 10. Humeral Extension and Adduction | Body: Stand on involved side<br>Stabilizing Hand: on posterior scapula<br>Action Hand: around involved wrist | Prone with elbow extended<br>Sidebend to involved side<br>Internally rotate humerus<br>Extend then adduct the involved humerus | Desired Stress: End Range Extension and Adduction of the humerus |
| 11. Humeral Internal Rotation | Body: Stand on involved side<br>Stabilizing Hand: anterior-inferior side of involved shoulder<br>Action Hand: Around involved wrist<br>Brace involved elbow on thigh* | Supine, slide to edge of the table<br>Flex elbow 90 degrees<br>Abduct humerus 120 degrees<br>Fully internally rotate humerus | Desired Stress: End Range Internal Rotation |
| 12. Elbow Extension | Body: Stand on involved side<br>Stabilizing Hand: on posterior-medial side of distal humerus<br>Action Hand: around involved wrist<br>Brace involved humerus on thigh* | Supine with elbow extended<br>Abduct humerus 90 degrees<br>Fully pronate forearm<br>Fully extend the elbow | Desired Stress: End Range Elbow Extension |
| 13. Upward Rotation of the Scapula | Body: Stand on involved side<br>Stabilizing Hand: on top of head to maintain rotation<br>Action Hand: on underside of AC-joint at armpit | Supine with elbow flexed 90 degrees<br>Rotate head to uninvolved side<br>Externally rotate involved humerus<br>Abduct humerus to upwardly rotate the scapula | Desired Stress: End Range Upward Rotation of the Scapula |
| 14. Humeral Abduction | Body: Stand on involved side<br>Stabilizing Hand: superior to scapula to prevent upward rotation of scapula<br>Action Hand: Grab humerus above the elbow | Supine, slide to edge of the table<br>Flex elbow 90 degrees<br>Externally rotate humerus<br>Fully abduct humerus | Desired Stress: End Range Humeral Abduction |
| 15. Protraction of the Scapula | Body: Stand on involved side<br>Stabilizing Hand: across lower portion of uninvolved ribcage | Supine with elbow extended<br>Externally rotate humerus<br>Flex humerus 90 | Desired Stress: End Range Protraction with anterior tilt of the Scapula |

TABLE 2-continued

MSAS - Passive Shortening

| MSAS (Pattern Number) | Tester Position | Subject Position | Applied Force and/or Desired Stress |
|---|---|---|---|
| | Action Hand: Posterior to AC-joint to maintain protraction and downward rotation of the scapula | degrees Depress, and then protract the scapula through oblique plane | |
| 16. Horizontal Adduction | Body: Stand on involved side Stabilizing Hand: on anterior side of distal clavicle to maintain retraction of the scapula Action Hand: around involved wrist | Supine with elbow extended and head in headpiece with scapula off the table Internally rotate humerus Horizontally adduct the humerus Maintain retraction of the scapula | Desired Stress: End Range Horizontal Adduction of the Humerus |
| 17. Elbow Flexion | Body: Stand on involved side Stabilizing Hand: anterior shoulder at AC-joint Action Hand: Around involved wrist | Supine, slide to edge of the table Forearm in neutral Fully flex elbow | Desired Stress: End Range Elbow Flexion |
| 18. Hip Adduction | Body: stand at the base of the client Stabilizing Hand: uninvolved ankle Action Hand: grab involved ankle | Supine, flex and cross uninvolved leg and place foot against lateral side of uninvolved knee Fully adduct involved femur at the hip Hands behind head | Desired Stress: End range hip adduction |
| 19. Hip Abduction | Body: stand at the base of the client on involved side Stabilizing Hand: opposite ASIS Action Hand: grab involved ankle | Supine, legs straight Hands behind head Fully abduct the femur at the hip | Desired Stress: End Range Hip Abduction **Maintain knee extension |
| 20. Knee Extension | Body: Stand on involved side Stabilizing Hand: Brace involved thigh Action Hand: grab lower leg at ankle | Supine, hands behind head Flex hip to slight tissue tension, then extend knee | Desired Stress: End Range Knee Extension |
| 21. Knee Flexion | Body: stand on involved side Stabilizing Hand: grab involved midfoot on medial side Action Hand: posterior calcaneus on involved side | Supine, with hands behind head Flex involved hip 80° Slightly internally rotate and adduct femur Dorsiflex and fully internally rotate the foot Full knee flexion | Desired Stress: End Range Knee Flexion |
| 22. Posterior Tibialis: Fibular | Direction of Force: Adduction and Inversion | Starting Position: Prone Plantarflexion, Adduction and inversion of the foot | Desired Stress: End Range Adduction and Inversion of the Foot |
| 23. Soleus: Medial | Starting Position: Prone (knee flexion)* Plantarflexion, Adduction and inversion of foot | Direction of Force: Plantarflexion | Desired Stress: End Range Plantarflexion of foot |
| 24. Anterior Tibialis: Tibial | Starting Position: Prone Dorsiflexion and Inversion of foot | Direction of Force: Dorsiflexion of foot through the 1st ray | Desired Stress: End Range Dorsiflexion and Inversion of foot |
| 25. Peroneus Brevis: Lateral | | Starting Position: Supine Plantarflexion* and Abduction and eversion of the foot | Applied Force: Abduction and Eversion Desired Stress: End Range abduction and Eversion |
| 26. Peroneus Tertius: Lateral | | Starting Position: Supine Dorsiflexion, Abduction and Eversion of the foot | Applied Force: Dorsiflexion about the talocrural joint axis Desired Stress: End Range Dorsiflexion of the foot |
| 27. Peroneus Longus: Metatarsal | | Starting Position: Supine Plantarflexion, | Applied Force: Eversion of the foot through the 1st Ray |

TABLE 2-continued

MSAS - Passive Shortening

| MSAS (Pattern Number) | Tester Position | Subject Position | Applied Force and/or Desired Stress |
|---|---|---|---|
| | | Abduction and eversion of the foot | Desired Stress: End Range Plantarflexion and Eversion of 1st Ray |
| 28. Extensor Hallucis Longus: Fibular | | Starting Position: Supine Dorsiflexion, Abduction and Inversion of the foot | Applied Force: Dorsiflexion of Hallux Desired Stress: End Range dorsiflexion of the hallux |
| 29. Extensor Digitorum Longus: Lateral | | Starting Position: Supine Dorsiflexion, Abduction and Eversion of the foot | Applied Force: Individual Digital Extension Desired Stress: End Range Digital Extension |
| 30. Flexor Hallucis Longus: Fibular | | Starting Position: Supine Plantarflexion, Adduction and Inversion of the foot | Applied Force: Plantarflexion of hallux Desired Stress: End range Plantarflexion of the hallux |
| 31. Flexor Digitorum Longus: Lateral | | Starting Position: Supine Plantarflexion, Adduction and Inversion of the foot | Applied Force: Individual digital flexion Desired Stress: End Range Digital Flexion |
| 32. Longus Capitis | Body: Stand distal to the body Stabilizing Hand: on back of head uninvolved side Action Hand: on back of head on involved side | Supine, tuck chin Rotate head slightly 20° towards uninvolved side Flex cervical spine | Desired Stress: End Range Cervical flexion |
| 33. Multifidus Cervicis: Inferior | Body: Stand distal to the body Stabilizing Hand: on uninvolved side of head Action Hand: on involved side of head | Supine Head in neutral Fully rotate head | Desired Stress: End Range Cervical rotation |
| 34. Cervical Extension | Body: Stand on involved side of the body Stabilizing Hand: Posterior side of skull at midline: slide down to stabilize thoracic spine Action Hand: Anterior side of skull at midline | Prone, Extend head on neck Slightly rotate head to uninvolved side Fully extend neck and head | Desired Stress: End Range Cervical and Capital Extension |
| 35. Cervical Sidebend | Body: Stand distal to the body Stabilizing Hand: on involved side of head Action Hand: on uninvolved side of head | Supine, grab table on sides Rotate head to uninvolved side Fully Sidebend neck on thorax | Desired Stress: End Range Cervical Sidebend |
| 36. Extensor Carpi Radialis Longus: Abductor Division | Direction of Force: Extension | Starting Position: Supine Full Elbow flexion with forearm pronated Abduction/radial deviation of hand at wrist Wrist extension | Desired Stress: End range Extension and abduction/radial deviation of the wrist |
| 37. Flexor Carpi Radialis Longus: Abductor Division | Direction of Force: Flexion | Starting Position: Supine 90° Elbow flexion Grasp hand around thumb Abduct/radial deviate hand with Supination and full Wrist Flexion | Desired Stress: End Range Flexion and abduction/radial deviation of the wrist |
| 38. Anconeus: Ulnar Division | Direction of Force: Supination | Starting Position: Supine | Desired Stress: End Range Supination |

TABLE 2-continued

MSAS - Passive Shortening

| MSAS (Pattern Number) | Tester Position | Subject Position | Applied Force and/or Desired Stress |
|---|---|---|---|
| | | Elbow fully extended and Supination of the forearm | of the forearm |
| 39. Pronator Teres: Humeral Division | Direction of Force: Pronation | Starting Position: Supine Elbow fully extended and Pronation of the forearm | Desired Stress: End Range Pronation of the forearm |
| 40. Extensor Pollicis Longus: Ulnar Division | Direction of Force: Extension of the Thumb | Starting Position: Supine 90 degrees elbow flexion with wrist extension and forearm Supination and extension of IP and MP with abduction of CMC of the Thumb | Desired Stress: End Range Extension of the Thumb (driving radial deviation) |
| 41. Flexor Pollicis Longus | Direction of Force: Flexion of the thumb through the distal phalanx | Starting Position: Supine 90 degrees Elbow flexion with wrist flexion* and supination with flexion and adduction of the thumb | Desired Stress: End Range Flexion and adduction of the Thumb |
| 42. Extensor Digitorum: Medial Division | Direction of Force: Extension of each Digit (one at a time) | Starting Position: Supine | Desired Stress: End Range Extension of each Digit |
| 43. Flexor Digitorum Profundus: Medial Division | Direction of Force: Flexion of each Digit (one at a time) driving wrist flexion | Starting Position: Supine 90 degrees Elbow flexion with Supination and flexion of each digit (1 at a time) | Desired Stress: End Range Flexion of each Digit |

TABLE 3

Illustrative DFAMAT

| DFAMAT Pattern Number/Muscle | Origin | Insertion | Tips |
|---|---|---|---|
| 1 (Transverse Abdominis: Lower Fibers) | Thoraco-lumbar fascia, anterior ¾ of iliac crest and lateral inguinal ligament | Linea alba below umbilicus and into the pubic symphysis | Spinous process of T12-L5 and sacrum Anterior ¾ of iliac crest Inguinal ligament Superior to pubic bone Up linea alba to umbilicus |
| 2 (Internal Obliques: Anterior Fibers) | Lateral ⅔ of inguinal ligament and anterior iliac crest | With transverse abdominis into crest of pubis and into linea alba through an aponeurosis | Sidelying, palpate xyphoid process, down linea alba to umbilicis. Palpate from xyphoid process down and out along costal cartilage of ribs Palpate anterior ¾ of superior iliac crest Palpate spinous processes of T12-L5 |
| 3 (Exterior Obliques: Anterior Fibers) | Interdigitates surface of ribs 5-8 | Into linea alba through aponeurosis | Sidelying, use xyphoid process as landmark, move up and over to 5$^{th}$ rib, anterior to the serratus Palpate anterior aspect of ribs 5-8; angling back towards the spine Palpate superior/anterior ½ of ilium to ASIS Supine, palpate down aponeurosis and inguinal ligament |

TABLE 3-continued

Illustrative DFAMAT

| DFAMAT Pattern Number/Muscle | Origin | Insertion | Tips |
|---|---|---|---|
| 4 (Semispinalis Thoracis) | Arise from transverse process of all thoracic vertebrae | 1-10 thoracic and lower 4 cervical spinous processes | Spinous processes from C4 down to T10<br>Palpate transverse processes from C7-T1 to T12 |
| 5 (Transverse Abdominis: Upper Fibers) | Cartilage of lower 6 ribs | Linea alba superior to umbilicus | Supine, palpate xyphoid process, palpate along cartilage of ribs to angle<br>Down linea alba from xyphoid to umbilicus |
| 6 (Sternalis) | Manubrium and inferior-medial clavicle | Superior medial fascia of $4^{th}$ rectus | Supine, palpate at inferior-medial clavicle and moving 1 inch lateral on clavicle<br>Palpate superior-medial portion of $4^{th}$ section of the rectus abdominis |
| 7 (Rectus Abdominis; Fourth Section Lateral) | From $3^{rd}$ section of rectus abdominis | Into costal-cartilage of $6^{th}$ and $7^{th}$ rib | Supine, use xyphoid process as landmark, move across to anterior portion of $6^{th}$ & $7^{th}$ rib<br>Palpate down lateral aponeurosis and across inferior attachment<br>Palpate up linea alba to xyphoid process |
| 8 (Rectus Abdominis: Fourth Section: Medial) | From $3^{rd}$ section of rectus abdominis: lateral half | Into cartilage of $5^{th}$ rib and side of xyphoid process | Supine, use xyphoid process as landmark, move across and up to lower level of $5^{th}$ rib against sternum<br>Palpate down lateral aponeurosis and across inferior attachment<br>Palpate up linea alba to xyphoid process |
| 9 (PSOAS MINOR) | Anterior-lateral bodies of T12 & L1 (L2) vertebrae and associated disc | The pectineal line, the ilio-pectineal eminence and the iliac fascia | Xyphoid process to anterior body of T12, L1 & L2<br>Move down, palpate deep to superior ramus of pubis and inguinal ligament |
| 10 (Pyramidalis) | Front of pubis and anterior pubic ligament | Linea alba midway between pubic bone and umbilicus | Supine, palpate superior medial pubic bone<br>Up linea alba ⅓ up toward umbilicus<br>Angle downward to lateral pubis<br>Always palpating into muscle belly when working abdominal wall |
| 11 (Rectus Abdominis: First Division) | Inner origin of $2^{nd}$ section of rectus abdominis | Pubic crest and symphysis. Also lateral expansion to opposite side | Supine, use umbilicus as a landmark, find fascial line just below<br>Palpate across to aponeurosis<br>Follow downward to pubic bone<br>Across pubic bone and back up linea alba<br>Always palpating into muscle belly when working abdominal wall |
| 12 (Rectus Abdominis: Second Division) | From $1^{st}$ section of rectus abdominis | Into $2^{nd}$ section of rectus abdominis | Find bottom of $2^{nd}$ level<br>Palpate across, up side of aponeurosis<br>Palpate for superior fascia, palpate across and down linea alba<br>Always palpating into muscle belly when working abdominal wall |
| 13 (Rectus Abdominis: Third Section) | From $3^{rd}$ section of rectus abdominis | Into $4^{th}$ section of rectus abdominis | Supine, use umbilicus as landmark, find top of $2^{nd}$ |

TABLE 3-continued

Illustrative DFAMAT

| DFAMAT Pattern Number/Muscle | Origin | Insertion | Tips |
|---|---|---|---|
| | | | level |
| | | | Palpate across, up side of aponeurosis |
| | | | Palpate for superior fascia, palpate across and down linea alba |
| | | | Always palpating into muscle belly when working abdominal wall |
| 14 (PSOAS Major: Lumbar Fibers) | Bodies and Anterior surface of transverse processes of L2-L5 | Lesser trochanter of the femur | Supine, flex involved hip by bending knee and have client exhale |
| | | | Small circles to move abdominal contents to the side |
| | | | Active hip flexion to confirm |
| | | | Palpate L2-L5 transverse processes and bodies |
| | | | Palpate above adductor longus tendon into lesser trochanter |
| 15 (PSOAS Major Thoracic Fibers) | Bodies and transverse processes of T12 & L1 | Lesser trochanter of the femur | Supine, flex involved hip and have client exhale |
| | | | Small circles to move abdominal contents to the side |
| | | | Active hip flexion to confirm |
| | | | Palpate T12 & L1 transverse processes and bodies |
| | | | Palpate above adductor longus tendon into lesser trochanter |
| 16 (PSOAS Major: Diaphragmatic Fibers) | Right crus: upper 3 lumbar bodies<br>Left crus: upper 2 lumbar bodies | Central tendon; mid-central part of xyphoid process | Supine, palpate from xyphoid process to rib cage |
| | | | Have patient exhale to relax diaphragm and deflate lungs |
| | | | Press fingers into where diaphragm connects with thorax |
| | | | Palpate diaphragm down to angle of ribcage |
| | | | Palpate associated lumbar bodies |
| 17 (Iliacus) | Anterior surface of iliac crest | Lesser trochanter of femur | Supine, client flexes hip with femur externally rotated |
| | | | Curl fingers into iliac fossa |
| | | | Confirm through active hip flexion |
| | | | Palpate above adductor longus tendon into lesser trochanter |
| 18 (Iliacus Minor) | Anterior surface of iliac crest | Lesser trochanter of femur | Client flexes hip with femur externally rotated |
| | | | Curl fingers into iliac fossa palpating superficial belly |
| | | | Palpate above adductor longus tendon into lesser trochanter |
| 19 (Tensor Fascia Latae Posterior Fibers) | Anterior portion of outer lip of iliac crest | Into ilio-tibial tract just below joint capsule | Supine, up and into iliac crest posterior to ASIS |
| | | | Palpate at insertion into IT-Tract |
| | | | Superior portion of lateral condyle |

TABLE 3-continued

Illustrative DFAMAT

| DFAMAT Pattern Number/Muscle | Origin | Insertion | Tips |
|---|---|---|---|
| 20 (Tensor Fascia Latae Anterior Fibers) | Anterior portion of outer lip of iliac crest | Into ilio-tibial tract just below joint capsule | Palpate insertion of IT-band into lateral condyle of tibia<br>Supine, up and into iliac crest just off ASIS<br>Palpate at insertion into IT-tract<br>Superior portion of lateral condyle<br>Palpate insertion of IT-band into lateral condyle of tibia |

Example 2

Illustrative AMC&S Tests

1. Micro-Order 1, AMC&S Test
Transverse Abdominis Lower Fibers
Tester Position:
Body: Stand on uninvolved side
Stabilizing Hand: posterior-lateral side of involved ilium to hold end range spinal rotation
Action Hand: contact on medial side of involved knee maintain endrange rotation
Client Position:
Supine, Anchor thorax by wrapping arms around top of table
Head in headpiece
Flex hip to 90 degrees, with knee slightly flexed.
Cross lag across uninvolved thigh to create spinal rotation
Applied Force:
Maintain spinal rotation through stabilizing hand until testing force is applied
Counter rotation force through involved leg to create opposite side spinal rotation
Internal Oblique: Anterior
Tester Position:
Body: Stand on involved side
Leg across thigh
Stabilizing Hand: Grab uninvolved shoulder
Action Hand: anterior side of involved shoulder just below clavicle
    maintain end range rotation and neutral spine
Client Position:
Supine, Flex trunk to 90 degrees with feet on the table and knees slightly bent
Feet shoulder width apart
Cross arms across chest and raise elbows to 90 degrees of shoulder flexion in order to maintain spinal neutral
Fully rotate trunk to involved side while maintaining spinal neutral
Applied Force:
Extension through same side rotation
External Oblique: Anterior AMC&S Test
Tester Position:
Body: Stand on uninvolved side
Leg across thigh
Stabilizing Hand: Grab involved shoulder
Action Hand: anterior side of involved shoulder just below clavicle
    maintain end range rotation and neutral spine
Client Position:
Supine, flex trunk to 90 degrees with feet on the table and knees slightly bent
Feet shoulder width apart
Cross arms across chest and raise elbows to 90 degrees of shoulder flexion in order to maintain spinal neutral
Fully rotate trunk to opposite side while maintaining spinal neutral
Applied Force:
Counter-rotation
Semispinalis Thoracis
Tester Position:
Body: Stand on same side of muscle being tested
Leg over posterior hip across to involved side
Grab anterior aspect of both shoulders to assist in extension and opposite rotation
Stabilizing Hand: Maintain end range extension and rotation by holding uninvolved side shoulder up
Action Hand: move hand to posterior shoulder on uninvolved side
Client Position:
Prone, arms to side
Extend and fully rotate thorax to opposite side
Applied Force:
Counter-rotation
Transverse Abdominis: Upper
Tester Position:
Body: Stand on uninvolved side
Leg across thigh
Stabilizing hand: under mid-thoracic spine to assist in extension and rotation of spine
Action Hand: Grab posterior aspect of involved shoulder to maintain opposite rotation: shift to anterior side of involved shoulder just below clavicle
Client Position:
Supine, feet shoulder width apart
Cross arms across chest
Flex trunk 20 degrees with feet on table
Fully rotate trunk to opposite side while maintaining neutral position of the spine
Applied Force:
Counter-rotation
Sternalis
Tester Position:
Body: Stand on uninvolved side
Leg across thigh
Stabilizing hand: under mid-thoracic spine to assist in opposite rotation Action Hand: Grab posterior aspect of involved shoulder to maintain opposite rotation: shift to anterior side of involved shoulder just below clavicle
Client Position:
Supine, feet on the table and knees slightly bent
Feet shoulder width apart
Cross arms across chest
Crunch up through thoracic spine to flex trunk 20 degrees
Fully rotate trunk to opposite side
Fully exhale
Applied Force:
Counter-rotation force
Rectus Abdominis: 4th Lateral
Tester Position:
Body: Stand on uninvolved side
Leg across thigh
Stabilizing hand: under mid-thoracic spine to assist in extension and rotation of spine
Action Hand: Grab posterior aspect of involved shoulder to maintain opposite rotation: shift to anterior side of involved shoulder just below clavicle
Client Position:
Supine, feet on the table with knees slightly bent
Feet shoulder width apart
Cross and raise arms from chest
Flex trunk 45 degrees
Fully rotate trunk to opposite side while maintaining spinal neutral
Applied Force:
Counter-rotation
Rectus Abdominis: 4th Medial
Tester Position:
Body: Stand on involved side
Leg across thigh
Stabilizing hand: under mid-thoracic spine to assist in extension of spine
Action Hand: Anterior side of involved shoulder just below clavicle
Client Position:
Supine, with feet on the table and knees slightly bent
Feet shoulder width apart
Cross and raise arms from chest
Flex trunk 45 degrees
Slightly rotate trunk to opposite side while maintaining spinal neutral
Applied Force:
Extension
2. Micro-Order 2, AMC&S Test
Psoas Minor
Tester Position:
Body: Stand on involved side
Stabilizing Hand: Stabilize under involved glute/sacrum in order to maintain posterior pelvic tilt
Action Hand: wrap around ankle
Client Position:
Supine, Anchor thorax by wrapping arms around top of table
Externally rotate involved leg
Flex and slightly adduct hip toward midline of the body (maintaining external rotation of the femur) to drive a posterior pelvic tilt and spinal flexion
Applied Force:
Extend and slightly abduct thigh through oblique plane to create anterior pelvic tilt and spinal extension
Pyramidalis
Tester Position:
Body: Stand on involved side
Leg across shin**
Stabilizing Hand: stabilize across back guiding thorax into end range of trunk and spinal flexion
Action Hand: anterior side of involved shoulder just below clavicle
Client Position:
Supine, with feet on the table and knees slightly bent
Feet shoulder width apart
Reach arms behind back
Fully flex trunk and spine
Slightly rotate trunk to opposite side
Applied Force:
Extension
Rectus Abdominis: 1st
Tester Position:
Body: Stand on involved side
Leg across thigh
Stabilizing Hand: stabilize across back guiding thorax into end range of spinal flexion
Action Hand: anterior side of involved shoulder just below clavicle
Client Position:
Supine, with feet on the table and knees slightly bent:
Feet shoulder width apart
Cross arms across chest
Flex trunk 90 degrees
Slouch shoulders downwards to enhance spinal flexion
Slightly rotate trunk to opposite side
Applied Force:
Extension
Rectus Abdominis: 2nd
Tester Position:
Body: Stand on involved side
Leg across thigh
Stabilizing Hand: stabilize across back guiding thorax to maintain spinal neutral
Action Hand: anterior side of involved shoulder just below clavicle
Client Position:
Supine, with feet on the table and knees slightly bent
Feet shoulder width apart
Cross and raise arms from chest
Flex trunk 90 degrees
Slightly rotate trunk to opposite side while maintaining spinal extension
Applied Force:
Extension
Rectus Abdominis: 3rd
Tester Position:
Body: Stand on involved side
Leg across thigh
Stabilizing Hand: stabilize across back guiding thorax to maintain spinal neutral
Action Hand: anterior side of involved shoulder just below clavicle
Client Position:
Supine, with feet on table and knees slightly bent
Feet shoulder width apart
Cross and raise arms from chest
Flex trunk 75 degrees
Slightly rotate trunk to opposite side while maintaining spinal neutral
Applied Force:
Extension
3. Micro Order 3, AMC&S Test
Psoas Major: Lumbar Fibers Tester Position:
Body: Stand on involved side
Stabilizing Hand: Stabilize anterior side of involved thigh to maintain knee extension
Move to opposite ASIS
Action Hand: grab lower leg at ankle
Client Position:
Supine, Anchor thorax by wrapping arms around top of table
Externally rotate involved leg
Fully abduct leg, maintaining external rotation and knee extension
Flex and adduct leg through oblique plane toward opposite thorax
Applied Force:
Hip Extension and abduction through oblique plane
Psoas Major: Thoracic Fibers
Tester Position:
Body: Stand on involved side
Stabilizing Hand: Stabilize anterior side of involved thigh to maintain knee extension, switch to opp ASIS
Action Hand: grab lower leg at ankle
Client Position:
Supine, Anchor thorax by wrapping arms around top of table
Externally rotate involved leg
Fully abduct leg, maintaining external rotation and knee extension
Flex hip 30 degrees
Applied Force:
Hip Extension
Psoas Major: Diaphragmatic
Tester Position:
Body: Stand on involved side
Stabilizing Hand: Stabilize anterior side of involved thigh to maintain knee extension: switch to opp ASIS
Action Hand: grab lower leg at ankle
Client Position:
Supine, Anchor thorax by wrapping arms around top of table
Externally rotate involved leg
Fully abduct leg, maintaining external rotation and knee extension
Flex hip 10 degrees
Applied Force:
Hip Extension
Iliacus
Tester Position:
Body: Stand on involved side
Leg across thigh
Stabilizing Hand: Stabilize anterior side of involved thigh to maintain knee extension
Action Hand: grab lower leg at ankle
Client Position:
Supine, Anchor thorax by wrapping arms around top of table
Externally rotate involved leg Fully flex hip maintaining external rotation and knee extension
Applied Force:
Hip Extension
Iliacus Minor
Tester Position:
Body: Stand on uninvolved side*
Stabilizing Hand: Stabilize anterior side of involved thigh to maintain knee extension
Action Hand: grab lower leg at ankle
Client Position:
Supine, anchor thorax by wrapping arms around end of table
Externally rotate leg
Fully flex then adduct leg through oblique plane maintaining external rotation and knee extension
Applied Force:
Hip Extension and abduction through the oblique plane
Tensor Fascia Latae: Posterior Fibers
Tester Position:
Body: Stand on involved side
Stabilizing Hand: Stabilize anterior side of involved thigh to maintain knee extension
Action Hand: grab lower leg at ankle
Client Position:
Supine, Anchor thorax by wrapping arms around top of table
Internally rotate involved leg
Fully abduct involved leg, maintaining internal rotation and knee extension
Fully flex hip from abducted position
Applied Force:
Hip Extension
Tensor Fascia Latae Anterior Fibers
Tester Position:
Body: Stand on involved side
Stabilizing Hand: Stabilize anterior side of involved thigh to maintain knee extension
Action Hand: grab lower leg at ankle
Client Position:
Supine, Anchor thorax by wrapping arms around top of table
Internally rotate involved leg
Fully abduct involved leg, maintaining internal rotation and knee extension
Fully flex hip from abducted position
Applied Force:
Hip Extension and adduction through the oblique plane
4. Micro Order 4, AMC&S Test
Obturator Externus
Tester Position:
Body: stand on involved side
Leg across opposite thigh
Stabilizing Hand: lateral side of involved knee
Action Hand: cup involved heel
Client Position:
Supine, Anchor thorax by wrapping arms around top of table
Flex involved hip
Fully externally rotate the femur at the hip with tibia just below parallel to the table
Applied Force:
Internal rotation
Quadratus Femoris
Tester Position:
Body: stand on involved side
Stabilizing Hand: lateral side of involved knee
Action Hand: cup involved heel
Client Position:
Supine, Anchor thorax by wrapping arms around top of table
Flex hip 75°,
Fully externally rotate the femur at the hip. Tibia parallel to the table
Applied Force:
Internal rotation
Piriformis Tester Position:
Body: stand on involved side
Stabilizing Hand: Involved PSIS
Action Hand: grab involved ankle
Client Position:
Prone, flex knee 90°
Abduct involved thigh to tissue tension
Fully externally rotate the femur at the hip
Applied Force:
Internal rotation
Gemellus Inferior
Tester Position:
Body: stand on involved side
Stabilizing Hand: Involved PSIS
Action Hand: grab involved ankle
Client Position:
Prone, flex knee 90°
Abduct thigh 30°
Drop knee off side of table to create 20° of hip flexion
Brace against thigh
Fully externally rotate the femur at the hip
Applied Force:
Internal rotation
Gemellus Superior
Tester Position:
Body: stand on involved side
Stabilizing Hand: Medial aspect of involved thigh (reach around)
Action Hand: grab involved ankle
Client Position:
Prone, flex knee 90°
Abduct thigh 30°
Drop knee off side of table to create 45° of hip flexion
Fully externally rotate the femur at the hip
Applied Force:
Internal rotation
Adductor Minimus
Tester Position:
Body: stand on involved side
Stabilizing Hand: Involved PSIS
Action Hand: grab involved ankle
Client Position:
Prone, legs straight
Flex knee 90°
Adduct involved leg to tissue tension
Fully externally rotate the femur at the hip
Applied Force:
Internal rotation
Obturator Internus
Tester Position:
Body: stand on involved side
Stabilizing Hand: uninvolved ASIS
Action Hand: lateral side of involved knee
Client Position:
Supine, slide to edge of the table on involved side
Flex knee 100 degrees to level of opposite knee
Place plantar aspect of foot against side of table
Flex, abduct and externally rotate femur at hip
Applied Force:
Flexion and Adduction
5. Micro Order 5, AMC&S Test
Longissimus Thoracis
Tester Position:
Body: Stand on uninvolved side
Stabilizing Hand: stabilize uninvolved thorax, up and in to inferior rib cage
Start by setting pelvis in neutral
Action Hand: reach arm under knees, grabbing inferior-lateral side of involved knee
Client Position:
Supine, slide body to the top of the uninvolved side of the table
Anchor uninvolved side arm around upper corner of table
Sidebend thorax on ilium
Cross involved side arm on chest
Take both legs to involved side to create end range spinal sidebend
Applied Force:
Opposite sidebend
Keep body flat in plane of the table
Longissimus Lumborum
Tester Position:
Body: Stand on uninvolved side
Stabilizing Hand: stabilize uninvolved ilium, up and in to inferior iliac crest
Start by setting pelvis in neutral
Action Hand: reach arm under knees, grabbing inferior-lateral side of involved knee
Client Position:
Supine, slide body to the top of the uninvolved side of the table
Anchor uninvolved side arm around upper corner of table
Sidebend thorax on ilium
Cross involved side arm on chest
Take both legs to involved side to create end range spinal sidebend
Applied Force:
Opposite sidebend
Keep body flat in plane of the table
Internal Oblique: Lateral
Tester Position:
Body: Stand on involved side
Stabilizing Hand: stabilize involved thigh
Action Hand: Lateral side of involved shoulder
Client Position:
Supine, with feet on table with knees slightly bent
Feet shoulder width apart
Cross arms
Flex trunk 90 degrees
Fully rotate trunk to opposite side
Laterally bend at trunk through plane of shoulders toward involved side
Applied Force:
Opposite sidebend: through plane of shoulders
External Oblique: Lateral
Tester Position:
Body: Stand on uninvolved side
Stabilizing Hand: stabilize uninvolved ilium pressing up and in to iliac crest
Action Hand: reach arm under knees, grabbing inferior-lateral side of involved knee
Client Position:
Supine, Cross arms on chest
Elevate legs 20 degrees with knees straight
Take both legs to involved side to create end range spinal sidebend
Applied Force:
Opposite sidebend
Keep body flat in plane of the table
Iliocostalis Thoracis
Tester Position:
Body: Stand on uninvolved side
Stabilizing Hand: stabilize uninvolved thorax pressing up and in to inferior rib cage Action Hand: reach arm under knees, grabbing inferior-lateral side of involved knee
Client Position:
Supine, legs straight
Internally rotate leg on involved side
Cross arms on chest
Take both legs to involved side to create end range spinal sidebend
Applied Force:
Opposite sidebend
Keep body flat in plane of the table
Iliocostalis Lumborum
Tester Position:
Body: Stand on uninvolved side
Stabilizing Hand: stabilize uninvolved ilium pressing up and in to inferior iliac crest
Action Hand: reach arm under knees, grabbing inferior-lateral side of involved knee
Client Position:
Supine, legs straight
Internally rotate leg on involved side
Cross arms on chest
Take both legs to involved side to create end range spinal sidebend
Applied Force:
Opposite sidebend
Keep body flat in plane of the table
Multifidus: Thoraco-Lumbar
Tester Position:
Body: Stand on uninvolved side
Stabilizing Hand: stabilize uninvolved thorax pressing up and in to inferior rib cage
Action Hand: reach arm under knees, grabbing inferior-lateral side of involved knee
Client Position:
Supine, legs straight
Externally rotate leg on involved side
Cross arms on chest
Take both legs to involved side to create end range spinal sidebend
Applied Force:
Opposite sidebend
Keep body flat in plane of the table
Multifidus: Lumbo-Sacral
Tester Position:
Body: Stand on uninvolved side
Stabilizing Hand: stabilize uninvolved ilium pressing up and in to inferior iliac crest
Action Hand: reach arm under knees, grabbing inferior-lateral side of involved knee
Client Position:
Supine, legs straight
Externally rotate leg on involved side
Cross arms on chest
Take both legs to involved side to create end range spinal sidebend
Applied Force:
Opposite sidebend Keep body flat in plane of the table
Quadratus Lumborum Spinal Fibers
Tester Position:
Body: Stand on uninvolved side
Stabilizing Hand: stabilize uninvolved ilium pressing up and in to inferior iliac crest
Action Hand: reach arm under knees, grabbing inferior-lateral side of involved knee
Client Position:
Supine, legs straight
Cross arms on chest
Take both legs to involved side to create end range spinal sidebend
Applied Force:
Opposite sidebend
Keep body flat in plane of the table
Serratus Posterior: Inferior
Tester Position:
Body: Stand on involved side
Stabilizing Hand: stabilize involved thigh
Action Hand: Lateral side of involved shoulder
Client Position:
Supine, feet on table with knees slightly bent
Feet shoulder width apart
Cross arms
Flex trunk 90 degrees
Fully rotate trunk to involved side
Laterally bend at trunk through plane of shoulders toward involved side
Fully exhale
Applied Force:
Opposite sidebend: through plane of shoulders
Serratus Posterior: Superior
Tester Position:
Body: Stand on same side of muscle being tested
Leg across hip to brace involved side
Grab anterior aspect of both shoulders to assist in extension and opposite rotation
Stabilizing Hand: Maintain end range extension and rotation by holding involved side shoulder up
Action Hand: move hand to posterior shoulder on uninvolved side
Client Position:
Prone, arms to side
Fully extend and rotate thorax to opposite side
Fully exhale
Applied Force:
Counter-rotation
Quadratus Lumborum Costal Fibers
Tester Position:
Body: Stand on uninvolved side
Stabilizing Hand: stabilize uninvolved ilium pressing up and in to inferior iliac crest
Action Hand: reach arm under knees, grabbing inferior-lateral side of involved knee
Client Position:
Supine, legs straight
Cross arms on chest
Take both legs to involved side to create 10 degrees of spinal sidebend*
Applied Force:
Opposite sidebend
Keep body flat in plane of the table
6. Micro Order 6, AMC&S Test
Levator Scapula Superior Division
Tester Position:
Body: Stand on involved side
Stabilizing Hand: posterior-lateral side of involved wrist to maintain humeral external rotation and downward rotation of the scapula
Action Hand: Medial side of involved elbow
Client Position:
Supine, slide to edge of the table to allow scapula to retract off the side of the table
Rotate head to ipsilateral side Flex elbow 90 degrees
Externally rotate and adduct humerus
Downwardly rotate the scapula
Applied Force:
Abduct humerus to upwardly rotate the scapula
Levator Scapula Inferior Division
Tester Position:
Body: Stand on involved side
Stabilizing Hand: posterior-lateral side of involved wrist to maintain humeral external rotation and downward rotation of the scapula
Action Hand: Medial side of involved elbow
Client Position:
Supine, slide to edge of the table to allow scapula to retract off the side of the table
Rotate head to ipsilateral side
Flex elbow 90 degrees
Adduct humerus
Downwardly rotate the scapula
Applied Force:
Abduct humerus to upwardly rotate the scapula
Rhomboid Minor
Tester Position:
Body: Stand on involved side
Stabilizing Hand: posterior-lateral side of involved wrist to maintain humeral external rotation and downward rotation of the scapula
Action Hand: Medial side of involved elbow
Client Position:
Supine with elbow flexed to 90 degrees
Abduct humerus 20 degrees
Externally rotate humerus
Downwardly rotate the scapula
Applied Force:
Abduct humerus to upwardly rotate the scapula
Rhomboid Major
Tester Position:
Body: Stand on involved side
Stabilizing Hand: posterior-lateral side of involved wrist to maintain humeral external rotation and downward rotation of the scapula
Action Hand: Medial side of involved elbow
Client Position:
Supine, slide to edge of the table to allow scapula to retract off the side of the table
Flex elbow 90 degrees
Abduct humerus 20 degrees
Downwardly rotate the scapula
Applied Force:
Abduct humerus to upwardly rotate the scapula
7. Micro Order 7, AMC&S Test
Infraspinatus Superior Fibers
Tester Position:
Body: Stand on involved side
Stabilizing Hand: posterior-lateral side of involved shoulder
Action Hand: Around involved wrist
Brace involved elbow on thigh*
Client Position:
Supine, slide to edge of the table
Flex elbow 90 degrees
Adduct humerus 120 degrees
Fully externally rotate humerus
Applied Force:
Internally rotate humerus
Infraspinatus Superior-Middle Fibers
Tester Position:
Body: Stand on involved side
Stabilizing Hand: posterior-lateral side of involved shoulder
Action Hand: Around involved wrist
Brace involved elbow on thigh*
Client Position:
Supine, slide to edge of the table
Flex elbow 90 degrees
Adduct humerus 90 degrees
Fully externally rotate humerus
Applied Force:
Internally rotate humerus
Infraspinatus Inferior-Middle Fibers
Tester Position:
Body: Stand on involved side
Stabilizing Hand: posterior-lateral side of involved shoulder
Action Hand: Around involved wrist
Brace involved elbow on thigh*
Client Position:
Supine, slide to edge of the table
Flex elbow 90 degrees
Abduct humerus 45 degrees
Fully externally rotate humerus
Applied Force:
Internally rotate humerus
Infraspinatus Inferior Fibers
Tester Position:
Body: Stand on involved side
Stabilizing Hand: posterior-lateral side of involved shoulder
Action Hand: Around involved wrist
Brace involved elbow on thigh*
Client Position:
Supine, slide to edge of the table
Flex elbow 90 degrees
Abduct humerus 30 degrees
Fully externally rotate humerus
Applied Force:
Internally rotate humerus
Teres Minor
Tester Position:
Body: Stand on involved side
Stabilizing Hand: posterior-lateral side of involved shoulder
Action Hand: Around involved wrist
Brace involved elbow on thigh*
Client Position:
Supine, slide to edge of the table
Flex elbow 90 degrees
Adduct humerus
Fully externally rotate humerus
Applied Force:
Internally rotate humerus
8. Micro Order 8, AMC&S Test
Intertransversarii
Tester Position:
Body: Stand on same side of muscle being tested**
Grab anterior aspect of both arms to assist in extension and opposite rotation
Stabilizing Hand: Maintain end range extension and rotation by holding uninvolved side shoulder up and back
Action Hand: move hand to posterior-inferior thorax on uninvolved side
Leg across involved thigh to stabilize pelvis Client Position:
Prone, hands behind head
Fully extend and rotate thorax to opposite side
Applied Force:
Flexion
Interspinalis Lumborum
Tester Position:
Body: Stand on same side of muscle being tested
Grab anterior aspect of both arms to assist in extension
Stabilizing Hand: Maintain end range extension by holding involved side shoulder up*
Action Hand: move hand to posterior-inferior thorax on involved side
Leg across involved thigh to stabilize pelvis
Client Position:
Prone, hands behind head
Fully extend spine
Applied Force:
Flexion
Spinalis Thoracis
Tester Position:
Body: Stand on uninvolved side
Stabilizing Hand: stabilize uninvolved thorax pressing up and in to inferior rib cage
Action Hand: reach arm under knees, grabbing inferior-lateral side of involved
Client Position:
Supine, legs straight
Legs together, arch spine
Cross arms on chest
Take both legs to involved side to create end range spinal sidebend
Applied Force:
Opposite sidebend
Keep body flat in plane of the table
Spinalis Lumborum
Tester Position:
Body: Stand on uninvolved side
Stabilizing Hand: stabilize uninvolved ilium pressing up and in to inferior iliac crest
Action Hand: reach arm under knees, grabbing inferior-lateral side of involved knee
Client Position:
Supine, legs straight
Legs together, arch spine
Cross arms on chest
Take both legs to involved side to create end range spinal sidebend
Applied Force:
Opposite sidebend
Keep body flat in plane of the table
Rotatores Thoracis
Tester Position:
Body: Stand on uninvolved side
Anchor Leg across uninvolved thigh*
Stabilizing Hand: stabilize under involved side thorax
Action Hand: brace posterior shoulder on uninvolved side
Client Position:
Seated with lower legs off table
Flex trunk 90 degrees
Cross arms
Extend through thoracic spine
Slightly rotate to opposite side
Applied Force:
Flexion
Rotatores Lumborum
Tester Position:
Body: Stand on uninvolved side
Anchor leg across uninvolved thigh
Stabilizing Hand: stabilize across involved side ASIS
Action Hand: brace posterior shoulder on uninvolved side
Client Position:
Seated with lower legs off table
Flex trunk 90 degrees
Cross arms
Extend through lumbar spine
Slightly rotate to opposite side
Applied Force:
Flexion
9. Micro Order 9, AMC&S Test
Gluteus Maximus: Iliac
Tester Position:
Body: stand on involved side
Stabilizing hand: anterior, lower ⅓rd of involved thigh
Action hand: posterior, lower ⅓rd of involved thigh**
Client Position:
Prone, 90 degrees of knee flexion
Abduct thigh to tissue tension
Fully extend hip through plane of the thigh
Applied Force:
Hip flexion through plane of the thigh
Gluteus Maximus: Sacral
Tester Position:
Body: stand on involved side
Stabilizing hand: anterior, lower ⅓rd of involved thigh
Action hand: posterior, lower ⅓rd of involved thigh**
Client Position:
Prone, 90 degrees of knee flexion
Slight abduction of involved thigh
Fully extend hip
Applied Force:
Hip flexion
Gluteus Maximus Coccygeal
Tester Position:
Body: stand on involved side
Stabilizing hand: anterior, lower ⅓rd of involved thigh
Action hand: posterior, lower ⅓rd of involved thigh**
Client Position:
Prone, 90 degrees of knee flexion
Internally rotate involved thigh
Fully extend hip
Applied Force:
Hip flexion
10. Micro Order 10, AMC&S Test
Latissimus Dorsi Iliac Fibers
Tester Position:
Body: Stand on involved side
Stabilizing Hand: on posterior scapula
Action Hand: around involved wrist
Client Position:
Prone with elbow extended
Sidebend to involved side
Internally rotate humerus
Extend then adduct the involved humerus
Applied Force:
Abduction of the humerus
Latissimus Dorsi Lumbar Fibers
Tester Position:
Body: Stand on involved side
Stabilizing Hand: on posterior scapula
Action Hand: around involved wrist
Client Position:
Prone with elbow extended
Sidebend to involved side Internally rotate humerus
Extend the involved humerus
Applied Force:
Flexion of the humerus
Latissimus Dorsi Thoracic Fibers
Tester Position:
Body: Stand on involved side
Stabilizing Hand: on posterior scapula
Action Hand: around involved wrist
Client Position:
Prone with elbow extended
Sidebend to involved side
Internally rotate humerus
Extend and Adduct involved humerus
Applied Force:
Flexion and Abduction of the humerus through the oblique plane
Teres Major Inferior Fibers
Tester Position:
Body: Stand on involved side
Stabilizing Hand: on posterior side of involved scapula
Action Hand: posterior-medial side of involved elbow
Client Position:
Prone with elbow flexed 90 degrees Place involved hand on ipsilateral PSIS
Extend and horizontally abduct involved humerus
Applied Force:
Flexion and horizontal Adduction of the humerus
Teres Major Superior Fibers
Tester Position:
Body: Stand on involved side
Stabilizing Hand: on posterior side of involved scapula
Action Hand: posterior-medial side of involved elbow
Client Position:
Prone with elbow flexed 120 degrees
Place involved hand on ipsilateral thorax
Extend and horizontally abduct involved humerus
Applied Force:
Flexion and horizontal Adduction of the humerus
Tricep Long Head
Tester Position:
Body: Stand on involved side
Stabilizing Hand: on posterior scapula
Action Hand: around involved wrist
Client Position:
Prone with elbow extended
Palm down
Extend the involved humerus
Applied Force:
Flexion of the humerus
11. Micro Order 11, AMC&S Test
Sub Scapularis Superior Fibers
Tester Position:
Body: Stand on involved side
Stabilizing Hand: anterior-inferior side of involved shoulder
Action Hand: Around involved wrist
Brace involved elbow on thigh*
Client Position:
Supine, slide to edge of the table
Flex elbow 90 degrees
Abduct humerus 120 degrees
Fully internally rotate humerus
Applied Force:
Externally rotate humerus
Sub Scapularis Superior-Middle Fibers
Tester Position:
Body: Stand on involved side
Stabilizing Hand: anterior-inferior side of involved shoulder
Action Hand: Around involved wrist
Brace involved elbow on thigh*
Client Position:
Supine, slide to edge of the table
Flex elbow 90 degrees
Abduct humerus 90 degrees
Fully internally rotate humerus
Applied Force:
Externally rotate humerus
Sub Scapularis Inferior Fibers
Tester Position:
Body: Stand on involved side
Stabilizing Hand: anterior-inferior side of involved shoulder
Action Hand: Around involved wrist
Brace involved elbow on thigh*
Client Position:
Supine, slide to edge of the table
Flex elbow 90 degrees
Abduct humerus 30 degrees
Fully internally rotate humerus
Applied Force:
Externally rotate humerus
12. Micro Order 12, AMC&S Test
Tricep Medial Fibers
Tester Position:
Body: Stand on involved side
Stabilizing Hand: on posterior-medial side of distal humerus
Action Hand: around involved wrist
Brace involved humerus on thigh*
Client Position:
Supine with elbow extended
Abduct humerus 90 degrees
Fully pronate forearm
Fully extend the elbow
Applied Force:
Elbow flexion
Tricep Lateral Head
Tester Position:
Body: Stand on involved side
Stabilizing Hand: on posterior-medial side of distal humerus
Action Hand: around involved wrist
Brace involved humerus on thigh*
Client Position:
Supine with elbow extended
Abduct humerus 90 degrees
Fully supinate forearm
Fully extend the elbow
Applied Force:
Elbow flexion
Articularis Cubiti
Tester Position:
Body: Stand on involved side
Stabilizing Hand: anterior shoulder at AC-joint
Action Hand: around involved wrist
Client Position:
Supine with elbow flexed
Fully pronate forearm
Applied Force:
Elbow flexion 13. Micro Order 13, AMC&S Test
Upper Trapezius Clavicular Fibers
Tester Position:
Body: Stand on involved side
Stabilizing Hand: on underside of AC joint at armpit to maintain upward rotation of the scapula
Action Hand: around involved wrist
Client Position:
Supine with elbow extended
Rotate head to uninvolved side
Fully internally rotate the involved humerus to protract scapula
Abduct humerus then drive upward rotation of the scapula
Applied Force:
Adduction to downwardly rotate the scapula*
Upper Trapezius Scapular Fibers
Tester Position:
Body: Stand on involved side
Stabilizing Hand: on underside of AC joint at armpit to maintain upward rotation of the scapula
Action Hand: around involved wrist
Client Position:
Supine with elbow extended
Rotate head to uninvolved side Internally rotate involved humerus to protract scapula Flex and abduct involved humerus 45 degrees Upwardly rotate the scapula
Applied Force:
Adduction to downwardly rotate the scapula*
Middle Trapezius
Tester Position:
Body: Stand on involved side
Stabilizing Hand: on anterior side of AC joint to maintain retraction of the scapula
Action Hand: around involved wrist
Client Position:
Supine with elbow extended and head in headpiece with scapula off the table
Horizontal Abduction of the humerus to drive retraction of the scapula
Applied Force:
Horizontal Adduction to protract the scapula
Lower Trapezius
Tester Position:
Body: Stand on involved side
Stabilizing Hand: anterior to the AC joint
Action Hand: around involved wrist
Client Position:
Supine with elbow extended and head in headpiece with scapula off the table
Flexion and Horizontal Abduction of the humerus through the oblique plane to drive upward rotation and retraction of the scapula
Applied Force:
Extenson and Horizontal Adduction through the oblique plane to drive protraction and downward rotation of the scapula
Serratus Anterior Upper Fibers
Tester Position:
Body: Stand on involved side
Stabilizing Hand: on posterior-superior humerus to maintain protraction of the scapula
Action Hand: around involved wrist
Client Position:
Supine with elbow extended and palm up
Abduct humerus 90 degrees
Horizontally adduct involved humerus 45 degrees
Lift arm to drive protraction of the scapula
Applied Force:
Horizontal Abduction to retract the scapula
Serratus Anterior Lower Fibers
Tester Position:
Body: Stand on involved side
Stabilizing Hand: on underside of AC joint at armpit to maintain upward rotation of the scapula
Action Hand: around involved wrist
Client Position:
Supine with elbow extended and head in headpiece with scapula off the table
Palm up
Fully flex involved humerus
Applied Force:
Humeral Extension
Subclavius Lateral Fibers
Tester Position:
Body: Stand on involved side
Stabilizing Hand: on underside of AC joint at armpit to maintain upward rotation of the scapula
Action Hand: around involved wrist
Client Position:
Supine with elbow extended
Internally rotate humerus
Flex and fully abduct involved humerus
Upwardly rotate the scapula
Applied Force:
Adduction to downwardly rotate the scapula
Subclavius Medial Fibers
Tester Position:
Body: Stand on involved side
Stabilizing Hand: on underside of AC joint at armpit to maintain upward rotation of the scapula
Action Hand: around involved wrist
Client Position:
Supine, with elbow extended and palm up
Flex and fully abduct involved humerus
Upwardly rotate the scapula
Applied Force:
Humeral Adduction to downwardly rotate the scapula
14. Micro Order 14, AMC&S Test
Supraspinatus Fossa Division
Tester Position:
Body: Stand on involved side
Stabilizing Hand: Anterior to AC joint
Action Hand: around involved wrist
Client Position:
Supine with elbow extended
Fully internally rotate involved humerus to protract the scapula
Abduct humerus 30 degrees
Applied Force:
Adduct the humerus
Supraspinatus Spinal Division
Tester Position:
Body: Stand on involved side
Stabilizing Hand: Posterior* to the AC-joint
Action Hand: around involved wrist
Client Position:
Supine with elbow extended
Abduct humerus 30 degrees
Applied Force:
Adduct the humerus
Posterior Deltoid Medial Fibers
Tester Position:
Body: Stand on involved side
Stabilizing Hand: around involved wrist
Action Hand: Grab humerus above the elbow Client Position:
Supine, slide to edge of the table
Flex elbow 90 degrees
Fully internally rotate humerus
Horizontally abduct humerus 20 degrees
Abduct humerus to tissue tension
Applied Force:
Adduct humerus
Posterior Deltoid Lateral Fibers
Tester Position:
Body: Stand on involved side
Stabilizing Hand: around involved wrist
Action Hand: Grab humerus above the elbow
Client Position:
Supine, slide to edge of the table
Flex elbow 90 degrees
Fully internally rotate humerus
Abduct humerus to tissue tension
Applied Force:
Adduct humerus
Middle Deltoid Posterior Fibers
Tester Position:
Body: Stand on involved side
Stabilizing Hand: around involved wrist
Action Hand: Grab humerus above the elbow
Client Position:
Supine, slide to edge of the table
Flex elbow 90 degrees Slightly internally rotate humerus
Abduct humerus to tissue tension
Applied Force:
Adduct humerus
Middle Deltoid Anterior Fibers
Tester Position:
Body: Stand on involved side
Stabilizing Hand: around involved wrist
Action Hand: Grab humerus above the elbow
Client Position:
Supine, slide to edge of the table
Flex elbow 90 degrees
Slightly externally rotate humerus
Abduct humerus to tissue tension
Applied Force:
Adduct humerus
Anterior Deltoid Scapular Fibers
Tester Position:
Body: Stand on involved side
Stabilizing Hand: around involved wrist
Action Hand: Grab humerus above the elbow
Client Position:
Supine, slide to edge of the table
Flex elbow 90 degrees
Internally rotate humerus
Flex and abduct humerus toward ear
Applied Force:
Extend and Adduct humerus
Anterior Deltoid Clavicular Fibers
Tester Position:
Body: Stand on involved side
Stabilizing Hand: around involved wrist
Action Hand: Grab humerus above the elbow
Client Position:
Supine, slide to edge of the table
Flex elbow 90 degrees
Externally rotate humerus Flex and abduct humerus toward ear
Applied Force:
Extend and Adduct humerus
15. Micro Order 15, AMC&S Test
Pectoralis Minor Inferior Division
Tester Position:
Body: Stand on involved side
Stabilizing Hand: Posterior to AC-joint to maintain protraction and downward rotation of the scapula
Action Hand: around involved wrist
Client Position:
Supine with elbow extended
Externally rotate humerus
Flex humerus 90 degrees
Depress, then protract the scapula through oblique plane
Applied Force:
Flexion and horizontal abduction through the oblique plane to retract and posteriorly rotate the scapula
Pectoralis Minor Superior Division
Tester Position:
Body: Stand on involved side
Stabilizing Hand: Posterior to AC-joint to maintain protraction and downward rotation of the scapula
Action Hand: around involved wrist
Client Position:
Supine with elbow extended
Externally rotate humerus
Flex humerus 90 degrees
Depress, then protract the scapula through horizontal plane
Applied Force:
Horizontal abduction to retract the scapula
16. Micro Order 16, AMC&S Test
Pectoralis Major Sternal Fibers
Tester Position:
Body: Stand on involved side
Stabilizing Hand: on anterior side of distal clavicle to maintain retraction of the scapula
Action Hand: around involved wrist
Client Position:
Supine with elbow extended and head in headpiece with scapula off the table
Internally rotate humerus
Horizontally adduct the humerus
maintain retraction of the scapula
Applied Force:
Horizontal Abduction of the humerus
Pectoralis Major Clavicular Fibers
Tester Position:
Body: Stand on involved side
Stabilizing Hand: on anterior side of distal clavicle to maintain retraction of the scapula
Action Hand: around involved wrist
Client Position:
Supine with elbow extended and head in headpiece with scapula off the table
Internally rotate humerus
Horizontally adduct and flex the humerus through the oblique plane
Maintain retraction of the scapula
Applied Force:
Extend and horizontally abduct the humerus through the oblique plane
Pectoralis Major Costal Division
Tester Position:
Body: Stand on involved side
Stabilizing Hand: on anterior side of distal clavicle to maintain retraction of the scapula
Action Hand: around involved wrist Client Position:
Supine with elbow extended and head in headpiece with scapula off the table
Internally rotate humerus
Horizontally adduct and extend the humerus through the oblique plane
Maintain retraction of the scapula
Applied Force:
Flex and Horizontally Abduct the humerus through the oblique plane
Biceps Brachii Long Head
Tester Position:
Body: Stand on involved side
Stabilizing Hand: posterior humerus, superior to elbow
Action Hand: around involved wrist
Client Position:
Supine, with head in headrest and scapula off the table
Supinate forearm with elbow slightly flexed
Fully flex humerus
Applied Force:
Extend the humerus
Biceps Brachii Short Head
Tester Position:
Body: Stand on involved side
Stabilizing Hand: anterior shoulder inferior to AC joint
Action Hand: Around involved wrist
Client Position:
Supine, slide to edge of the table
Supinate forearm
Fully flex elbow
Applied Force:
Elbow extension
Coracobrachialis Superior Fibers
Tester Position:
Body: Stand on involved side
Stabilizing Hand: anterior to the AC joint*
Action Hand: around involved wrist
Client Position:
Supine with elbow extended Palm up
Abduct humerus 30 degrees
Flex humerus 20 degrees
Applied Force:
Extend the humerus
Coracobrachialis Inferior Fibers
Tester Position:
Body: Stand on involved side
Stabilizing Hand: Anterior to the AC-joint**
Action Hand: around involved wrist
Client Position:
Supine with elbow extended
Fully externally rotate humerus
Abduct humerus 30 degrees
Flex humerus 20 degrees
Applied Force:
Extend and abduct the humerus through the oblique plane
17. Micro Order 17, AMC&S Test
Brachialis
Tester Position:
Body: Stand on involved side
Stabilizing Hand: anterior shoulder at AC-joint
Action Hand: Around involved wrist
Client Position:
Supine, slide to edge of the table
Forearm in neutral
Fully flex elbow
Applied Force:
Elbow extension
Brachioradialis Superior Division
Tester Position:
Body: Stand on involved side
Stabilizing Hand: anterior shoulder at AC-joint
Action Hand: Around involved wrist
Client Position:
Supine, slide to edge of the table
Pronate forearm
Fully flex elbow
Applied Force:
Elbow extension
Brachioradialis Inferior Division
Tester Position:
Body: Stand on involved side
Stabilizing Hand: anterior shoulder at AC-joint
Action Hand: Around involved wrist
Client Position:
Supine, slide to edge of the table
Supinate forearm
Flex elbow 90 degrees
Applied Force:
Elbow extension
18. Micro Order 18, AMC&S Test
Adductor Magnus Oblique Fibers
Tester Position:
Body: stand at the base of the client on involved side
Stabilizing Hand: opposite ankle
Action Hand: grab involved ankle from above
    Do not force external rotation
Client Position:
Supine, legs straight
Hands behind head
Fully externally rotate involved femur
Move both legs to create end-range adduction on involved side
    Watch for pelvic hike
Applied Force:
Abduction
    maintain knee extension
Adductor Magnus Vertical Fibers
Tester Position:
Body: stand at the base of table
Stabilizing Hand: opposite ankle
Action Hand: grab involved ankle from below
Client Position:
Supine, legs straight
Hands behind head
Move both legs to create end-range adduction on involved side
    Watch for pelvic hike
Applied Force:
Abduction
    maintain knee extension
Adductor Longus Superior
Tester Position:
Body: stand at the base of the table
Stabilizing Hand: opposite ankle
Action Hand: grab involved ankle from below
Client Position:
Supine, legs straight
Hands across chest
Fully externally rotate involved femur
Flex hips: Femur 10 degrees from table
Move both legs to create end-range adduction on involved side
    Watch for pelvic hike Applied Force:
Abduction
   maintain knee extension
Adductor Longus Inferior
Tester Position:
Body: stand at the base of the table
Stabilizing Hand: opposite ankle
Action Hand: grab involved ankle from below
Client Position:
Supine, legs straight
Hands across chest
Flex hips: Femur 10 degrees from table
Move both legs to create end-range adduction on involved side
Applied Force:
Abduction
   maintain knee extension
Adductor Brevis
Tester Position:
Body: stand at the base of the table
Stabilizing Hand: opposite ankle
Action Hand: grab involved ankle from below
Client Position:
Supine, legs straight
Hands across chest
Fully internally rotate involved femur
Flex involved hip: Femur 10 degrees from table
Fully adduct the femur at the hip while maintaining internal rotation
   Watch for pelvic rotation
Applied Force:
Abduction
   maintain knee extension
Pectineus
Tester Position:
Body: stand at the base of the client
Stabilizing Hand: opposite ankle
Action Hand: grab involved ankle
Client Position:
Supine, legs straight
Hands across chest
Fully externally rotate involved femur
Flex the involved hip 30 degrees
Adduct to midline while maintaining external rotation
Applied Force:
Extension and Abduction through the oblique plane
   maintain knee extension
Gracilis
Tester Position:
Body: stand at the base of the client on involved side
Stabilizing Hand: opposite ankle
Action Hand: grab involved ankle from below
Client Position:
Supine, legs straight
Hands behind head
Fully internally rotate involved femur
Move both legs to create end-range adduction on involved side
Applied Force:
Abduction
   maintain knee extension
19. Micro Order 19, AMC&S Test
Gluteus Medius Anterior Fibers
Tester Position:
Body: stand at the base of the client on involved side
Stabilizing Hand: opposite ASIS or thigh
Action Hand: grab involved ankle
Client Position:
Supine, legs straight
Hands behind head
Fully internally rotate involved femur
Fully abduct the femur at the hip while maintaining internal rotation
Applied Force:
Adduction
   Maintain knee extension
Gluteus Medius Posterior Fibers
Tester Position:
Body: stand at the base of the client on involved side
Stabilizing Hand: opposite ASIS or thigh
Action Hand: grab involved ankle
Client Position:
Supine, legs straight
Hands behind the head
Fully externally rotate involved femur
Fully abduct the femur at the hip while maintaining external rotation
Applied Force:
Adduction
   Maintain knee extension
Gluteus Medius Middle Fibers
Tester Position:
Body: stand at the base of the client on involved side
Stabilizing Hand: opposite ASIS or thigh
Action Hand: grab involved ankle
Client Position:
Supine, legs straight
Hands behind the head
Fully abduct the femur at the hip
Applied Force:
Adduction
   Maintain knee extension
Gluteus Minimus Anterior Fibers
Tester Position:
Body: stand at the base of the client on involved side
Stabilizing Hand: opposite ASIS or thigh
Action Hand: grab involved ankle
Client Position:
Supine, legs straight
Hands behind the head
Fully internally rotate involved femur
Flex hip 25 degrees
Fully abduct the femur at the hip while maintaining internal rotation
Applied Force:
Adduction
   Maintain knee extension
Gluteus Minimus Lateral Fibers
Tester Position:
Body: stand at the base of the client on involved side
Stabilizing Hand: opposite ASIS or thigh
Action Hand: grab involved ankle
Client Position:
Supine, legs straight
Hands behind the head
Fully externally rotate involved femur
Flex hip 25 degrees
Fully abduct the femur at the hip while maintaining external rotation
Applied Force:
Adduction
   Maintain knee extension 20. Micro Order 20, AMC&S Test
Rectus Femoris Straight Head
Tester Position:
Body: Stand on involved side
Stabilizing Hand: Brace involved thigh
Action Hand: grab lower leg at ankle
Client Position:
Supine, hands behind head
Fully flex hip with end range knee extension
Applied Force:
Hip Extension
Rectus Femoris Reflected Head
Tester Position:
Body: Stand on involved side
Stabilizing Hand: Brace involved thigh
Action Hand: grab lower leg at ankle
Client Position:
Supine, hands behind head
Internally rotate involved leg
Fully flex hip with end range knee extension
Applied Force:
Hip Extension
Vastus Intermedius: Medial
Tester Position:
Body: stand on involved side
Stabilizing Hand: posterior thigh behind knee joint
Action Hand: anterior tibia
Client Position:
Supine, hands behind head
Flex involved hip to tissue tension
Fully internally rotate involved tibia
Tibia parallel to table
Applied Force:
knee flexion
Vastus Intermedius: Lateral
Tester Position:
Body: stand on involved side
Stabilizing Hand: posterior thigh behind knee joint
Action Hand: anterior tibia
Client Position:
Supine, hands behind the head
Flex involved hip to tissue tension
Fully externally rotate involved tibia
Tibia parallel to table
Applied Force:
knee flexion
Vastus Medialis: Upper
Tester Position:
Body: stand on involved side
Stabilizing Hand: lateral side of involved knee
Action Hand: grab involved calcaneus
Client Position:
Supine, hands behind head
Flex hip 60° and flex knee 110° so that heel is at level of opposite knee
Fully externally rotate femur with slight abduction
Internally rotate tibia and plantarflex foot
Applied Force:
Internal rotation of femur at hip
Vastus Medialis: Middle
Tester Position:
Body: stand on involved side
Stabilizing Hand: lateral side of involved knee
Action Hand: grab involved calcaneus
Client Position:
Supine, hands behind head
Flex hip 45° and flex knee 75° so that heel is at opposite mid shin level
Fully externally rotate femur with slight abduction
Internally rotate tibia and plantarflex foot
Applied Force:
Internal rotation of femur at hip
Vastus Medialis: Lower
Tester Position:
Body: stand on involved side
Stabilizing Hand: lateral side of involved knee
Action Hand: grab involved calcaneus
Client Position:
Supine, hands behind head
Flex hip 20° and flex knee 20° so that heel is at level of opposite ankle
Fully externally rotate femur with slight abduction
Internally rotate tibia and plantarflex foot
Applied Force:
Internal rotation of femur at hip
Vastus Lateralis: Upper
Tester Position:
Body: stand on uninvolved side
Stabilizing Hand: medial side of involved knee
Action Hand: grab involved calcaneus
Client Position:
Supine, hands behind head
Flex hip 60° and flex knee 110° so that heel is at level of opposite knee
Fully internally rotate femur with slight adduction
Externally rotate tibia and plantarflex foot
Applied Force:
External rotation of femur at hip
Vastus Lateralis: Middle
Tester Position:
Body: stand on uninvolved side
Stabilizing Hand: medial side of involved knee
Action Hand: grab involved calcaneus
Client Position:
Supine, hands behind head
Flex hip 25° and flex knee 75° so that heel is at opposite mid shin level
Fully internally rotate femur with slight adduction
Externally rotate tibia and plantarflex foot
Applied Force:
External rotation of femur at hip
Vastus Lateralis: Lower
Tester Position:
Body: stand on uninvolved side
Stabilizing Hand: medial side of involved knee
Action Hand: grab involved calcaneus
Client Position:
Supine, hands behind head
Flex hip 20° and flex knee 20° so that heel is at level of opposite ankle
Fully internally rotate femur with slight adduction
Externally rotate tibia and plantarflex foot
Applied Force:
External rotation of femur at hip
Articularis Genu
Tester Position:
Body: stand on involved side
Stabilizing Hand: posterior side of involved knee
Action Hand: grab distal, anterior aspect of involved tibia
Client Position:
Supine, hands behind head
Flex hip 20° and flex knee 20°

Applied Force:
Hip extension while maintaining knee flexion
21. Micro Order 21, AMC&S Test
Semitendinosus
Tester Position:
Body: stand on involved side
Stabilizing Hand: grab involved midfoot on medial side
Action Hand: posterior calcaneus on involved side
Client Position:
Supine, with hands behind head
Flex involved hip 80°
Slightly internally rotate and adduct femur
Dorsiflex and fully internally rotate the foot
Full knee flexion
Applied Force:
knee extension
Semimembranosus Lateral
Tester Position:
Body: stand at base of table
Stabilizing Hand: grab involved midfoot on medial side
Action Hand: posterior calcaneus on involved side
Client Position:
Supine, with hands behind head
Flex involved hip 45°
Slightly externally rotate and abduct femur
Dorsiflex and fully internally rotate the foot
Flex knee 90°
Applied Force:
knee extension
Semimembranosus Medial
Tester Position:
Body: stand at base of table
Stabilizing Hand: grab involved midfoot on medial side
Action Hand: posterior calcaneus on involved side
Client Position:
Supine, with hands behind head
Flex involved hip 45°
Slightly internally rotate and adduct femur
Dorsiflex and fully internally rotate the foot
Flex knee 90°
Applied Force:
Knee extension
Bicep Femoris: Short head
Tester Position:
Body: stand on involved side
Stabilizing Hand: grab involved midfoot on medial side
Action Hand: posterior calcaneus on involved side
Client Position:
Supine, with hands behind head
Flex hip 80°
Slightly internally rotate and adduct femur
Dorsiflex and fully externally rotate the foot
Full knee flexion
Applied Force:
knee extension
Bicep Femoris: Long head Fibular
Tester Position:
Body: stand at base of table
Stabilizing Hand: grab involved midfoot on medial side
Action Hand: posterior calcaneus on involved side
Client Position:
Supine, with hands behind head
Flex involved hip 45°
Slightly internally rotate and adduct femur
Dorsiflex and fully externally rotate foot
Flex knee 90°
Applied Force:
knee extension
Bicep Femoris: Long head Tibial
Tester Position:
Body: stand at base of table
Stabilizing Hand: grab involved midfoot on medial side
Action Hand: posterior calcaneus on involved side
Client Position:
Supine, with hands behind head
Flex involved hip 45°
Dorsiflex and fully externally rotate foot
Flex knee 90°
Applied Force:
knee extension
Sartorius
Tester Position:
Body: stand on involved side
Stabilizing Hand: involved foot
Action Hand: Posterior aspect of distal tibia
Client Position:
Supine, with hands behind head
Flex knee 120 degrees
Flex, abduct and externally rotate femur at hip
Place ankle just above uninvolved knee
Internally rotate tibia
Applied Force:
Knee extension while maintaining abducted/externally rotated position
Popliteus
Tester Position:
Body: stand at base of table
Stabilizing Hand: grab calcaneus
Action Hand: medial forefoot
Client Position:
Supine
Flex involved hip and knee 45°
Internally rotate tibia through foot
Applied Force:
External rotation of the tibia through the foot
22. Micro Order 22, AMC&S Test
Posterior Tibialis Fibular Division
Client Position:
Supine, flex hip 45°, flex knee 90°
Plantarflexion and inversion of the foot.
Full adduction of the foot
Tester Position:
Body: stand at the base of the client
Stabilizing Hand: base of heel
Action Hand: medial aspect of the forefoot
Applied Force:
abduction of the foot
Posterior Tibialis Tibial Division
Client Position:
Supine, flex hip 45°, flex knee 90°
Plantarflexion of the foot.
Full adduction of the foot
Tester Position:
Body: stand at the base of the client
Stabilizing Hand: base of heel
Action Hand: medial aspect of the forefoot
Applied Force:
abduction of the foot
23. Micro Order 23, AMC&S Test
Medial Soleus
Client Position:
prone, knee flexed to 90°
adduction of the foot
full plantarflexion of the foot (point foot up and in)

Tester Position:
Body: stand on side of leg being tested
Stabilizing Hand: back of calcaneus
Action Hand: ball of foot (1st met head)
Applied Force:
dorsiflexion of the ankle about the talo-crual joint axis
Lateral Soleus
Client Position:
prone, knee flexed to 90°
Abduction of the foot
full plantarflexion of the foot (point foot up and out)
Tester Position:
Body: stand on side of leg being tested
Stabilizing Hand: back of calcaneus
Action Hand: ball of foot (4th and 5th met heads)
Applied Force:
dorsiflexion of the ankle about talo-crual joint axis
Lateral Gastroc
Client Position:
supine, flex hip 45°, flex knee 90°
External rotation of the foot
full ankle plantarflexion
   (point foot down and out)
Tester Position:
Body: stand at the base of the client
Stabilizing Hand: anterior, superior aspect of the forefoot
Action Hand: back of the calcaneus
Applied Force:
Knee extension
Medial Gastroc
Client Position:
supine, flex hip 45°, flex knee 90°
Internal rotation of the foot
full ankle plantarflexion
   (point foot down and in)
Tester Position:
Body: stand at the base of the client
Stabilizing Hand: anterior, superior aspect of the forefoot
Action Hand: back of the calcaneus
Applied Force:
Knee extension
Plantaris
Client Position:
supine, flex hip 45°, flex knee 90°
full ankle plantarflexion
   (point foot down)
Tester Position:
Body: stand at the base of the client
Stabilizing Hand: anterior, superior aspect of the forefoot
Action Hand: back of the calcaneus
Applied Force:
Knee extension
24. Micro Order 24, AMC&S Test
Anterior Tibialis Tibial Division
Client Position:
Supine, flex hip 45°, flex knee 90°
Adduction and inversion of the foot
Full dorsiflexion of the foot about the talocrural joint axis
   (through the 1st met)
Tester Position:
Body: stand at the base of the client
Stabilizing Hand: base of heel
Action Hand: Superior, medial aspect of the forefoot
Applied Force:
Plantarflexion of the foot about the talo-crural joint axis
Anterior Tibialis Interosseous Division Client Position:
Supine, flex hip 45°, flex knee 90°
Inversion of the foot
Full dorsiflexion of the foot about the talocrural joint axis
   (through the 1st met)
Tester Position:
Body: stand at the base of the client
Stabilizing Hand: base of heel
Action Hand: Superior, medial aspect of the forefoot
Applied Force:
Plantarflexion of the foot about the talo-crural joint axis
25. Micro Order 25, AMC&S Test
PERONEUS BREVIS Lateral division
Client Position:
Supine, flex hip 45°, flex knee 90°
Plantarflexion, abduction and eversion of the foot
Tester Position:
Body: stand at the base of the client
Stabilizing Hand: base of heel
Action Hand: lateral aspect of the forefoot
Applied Force:
Adduction of the foot
Peroneus Brevis Posterior Division
Client Position:
supine, flex hip 45°, flex knee 90°
Plantarflexion and abduction of the foot
Slight eversion of the foot
Tester Position:
Body: stand at the base of the client
Stabilizing Hand: base of heel
Action Hand: lateral aspect of the forefoot
Applied Force:
Adduction through the plane of foot
26. Micro Order 26, AMC&S Test
Peroneus Tertius Lateral Division
Client Position:
Supine, flex hip 45°, flex knee 90°,
Abduction & eversion of the foot
Full dorsiflexion of the foot about talo-crural joint axis
Tester Position:
Body: stand at the base of the client
Stabilizing Hand: base of heel
Action Hand: Superior, lateral aspect of the forefoot
Applied Force:
Plantarflexion of the foot about the talo-crural joint axis
Peroneus Tertius Anterior Division
Client Position:
Supine, flex hip 45°, flex knee 90°
Eversion of the foot
Full dorsiflexion of the foot about the talo-crural joint axis
Tester Position:
Body: stand at the base of the client
Stabilizing Hand: base of heel
Action Hand: Superior, lateral aspect of the forefoot
Applied Force:
Plantarflexion of the foot about the talo-crural joint axis
27. Micro Order 27, AMC&S Test
Peroneus Longus Metatarsal Division
Client Position:
supine, flex hip 45°, flex knee 90°
Plantarflexion, abduction and eversion of the foot.
Full plantarflexion and eversion of the 1st met
   (point foot down and out)
Tester Position:
Body: stand at the side of the client's involved foot
Stabilizing Hand: base of heel
Action Hand: Under 1st met head Applied Force:
Dorsiflexion and inversion of the foot (up and in) through the 1st metatarsal head
Peroneus Longus Cuneiform Division
Client Position:
supine, flex hip 45°, flex knee 90°
Plantarflexion and eversion of the foot
Full abduction of the foot
Tester Position:
Body: stand at the side of the client's involved foot
Stabilizing Hand: base of heel
Action Hand: lateral aspect of the forefoot
Applied Force:
adduction of the foot 28. Micro Order 28, AMC&S Test
Extensor Hallucis Longus Fibular Division
Client Position:
Supine, leg straight
Dorsiflexion with inversion of the foot.
Extension of the distal phalanx of hallux (driving ankle dorsiflexion)
Tester Position:
Body: Stand at base of the client
Stabilizing Hand: Brace proximal phalanx of hallux
Action Hand: brace dorsal surface of distal phalanx
Applied Force:
Plantarflexion of distal phalanx of hallux
do not force dorsiflexion of proximal phalanx
Extensor Hallucis Longus Interosseous Division
Client Position:
Supine, leg straight
Dorsiflexion of the foot
Extension of the distal phalanx of hallux (driving ankle dorsiflexion)
Tester Position:
Body: Stand at base of the client
Stabilizing Hand: Brace proximal phalanx of hallux
Action Hand: brace dorsal surface of distal phalanx
Applied Force:
Plantarflexion of distal phalanx of hallux
do not force dorsiflexion of proximal phalanx
Extensor Hallucis Brevis
Client Position:
Supine, leg straight
Dorsiflexion of the foot
Dorsiflexion of proximal phalanx of the hallux (driving ankle dorsiflexion)
Tester Position:
Body: Stand at base of the client
Stabilizing Hand: Brace 1st metatarsal head
Action Hand: brace proximal phalanx of hallux
Applied Force:
Plantarflexion of the proximal phalanx of the hallux 29. Micro Order 29, AMC&S Test
Extensor Digitorum Longus Lateral Division
Client Position:
Supine, leg straight
Dorsiflexion with eversion of the foot.
Extension of the middle and distal phalanges of lateral two toes (driving ankle dorsiflexion)
Tester Position:
Body: Stand at base of the client
Stabilizing Hand: Brace proximal phalanges of lateral 2 toes
Action Hand: brace dorsal surface of middle and distal phalanges of lateral 2 toes
Applied Force:
Simultaneous plantarflexion of the middle and distal phalanges of lateral 2 toes
do not force dorsiflexion of proximal phalanx
Extensor Digitorum Longus Medial Division
Client Position:
Supine, leg straight
Dorsiflexion with eversion of the foot.
Extension of the middle and distal phalanges of medial two toes (driving ankle dorsiflexion)
Tester Position:
Body: Stand at base of the client
Stabilizing Hand: Brace proximal phalanges of medial 2 toes
Action Hand: brace dorsal surface of middle and distal phalanges of medial 2 toes
Applied Force:
Simultaneous plantarflexion of middle and distal phalanges of the medial 2 toes
do not force dorsiflexion of proximal phalanx
Extensor Digitorum Brevis
Client Position:
Supine, leg straight
Dorsiflexion of foot
Dorsiflex proximal phalanx of 2nd, 3rd & 4th toes (driving ankle dorsiflexion)
Tester Position:
Body: Stand distal to body
Stabilizing Hand: Brace plantar surface of foot
Action Hand: brace dorsal surface of proximal phalanx of the middle 3 toes
Applied Force:
Plantarflexion of the proximal phalanx of the middle 3 toes
1st Dorsal Interossei
Client Position:
Supine, leg straight
Foot Neutral
Extend and abduct the proximal phalanx of the 2nd toe
Tester Position:
Body: Stand distal to body
Stabilizing Hand: Brace 2nd metatarsal
Action Hand: brace medial aspect of proximal phalanx of 2nd toe
Applied Force:
Adduction of the proximal phalanx of the 2nd toe toward the midline of foot*
2nd Dorsal Interossei
Client Position:
Supine, leg straight
Foot Neutral
Extend and abduct the proximal phalanx of the 2nd toe
Tester Position:
Body: Stand distal to body
Stabilizing Hand: Brace 2nd metatarsal
Action Hand: brace lateral aspect of proximal phalanx of 2nd toe
Applied Force:
Adduction of the proximal phalanx of 2nd toe toward the midline of the foot*
3rd Dorsal Interossei
Client Position:
Supine, leg straight
Foot neutral
Extend and abduct the proximal phalanx of the 3rd toe
Tester Position:
Body: Stand distal to body
Stabilizing Hand: Brace 3rd metatarsal Action Hand: brace lateral aspect of proximal phalanx of 3rd toe
Applied Force:
Adduction of the proximal phalanx of the 3rd toe toward the midline of the foot
4th Dorsal Interossei
Client Position:
Supine, leg straight
Foot Neutral
Extend and abduct the proximal phalanx of the 4th toe
Tester Position:
Body: Stand distal to body
Stabilizing Hand: Brace 4th metatarsal
Action Hand: brace lateral aspect of proximal phalanx of 4th toe
Applied Force:
Adduction of the proximal phalanx of the 4th toe toward the midline of the foot
30. Micro Order 30, AMC&S Test
Flexor Hallucis Longus Fibular Division
Client Position:
Supine, leg straight
Plantarflexion and inversion of the foot.
Full Plantarflexion of distal phalanx of the hallux (driving ankle plantarflexion)
(Point big toe down and in)
Tester Position:
Body: Stand to the side of involved foot
Stabilizing Hand: Brace proximal phalanx of the hallux
Action Hand: brace plantar surface of distal phalanx of the hallux
Applied Force:
Dorsiflexion of the distal phalanx of the hallux
do not force plantarflexion of proximal phalanx
Flexor Hallucis Longus Interosseous Division
Client Position:
Supine: leg straight
Plantarflexion of the foot
Full Plantarflexion of distal phalanx of the hallux (driving ankle plantarflexion)
(point big toe down)
Tester Position:
Body: Stand to the side of involved foot
Stabilizing Hand: Brace the proximal phalanx of the hallux
Action Hand: brace plantar surface of distal phalanx of the hallux
Applied Force:
Dorsiflexion of the distal phalanx of the hallux
do not force plantarflexion of proximal phalanx
Flexor Hallucis Brevis 1st Cuneiform Division
Client Position:
Supine, straight leg
Plantarflexion of the foot
Plantarflexion and Inversion of the proximal phalanx of the hallux (relative to midline of the foot)
Tester Position:
Body: Stand to the side of involved foot
Stabilizing Hand: Brace 1st metatarsal
Action Hand: brace the inferior, lateral aspect of the proximal phalanx of the hallux
Applied Force:
Dorsiflexion and Eversion of the proximal phalanx of the hallux (relative to midline of the foot)
Flexor Hallucis Brevis Cuboid Division
Client Position:
Supine, straight leg
Plantarflexion of the foot
Plantarflexion and Eversion of the proximal phalanx of the hallux (relative to midline of the foot)
Tester Position:
Body: Stand to the side of the involved foot
Stabilizing Hand: Brace the 1st metatarsal
Action Hand: brace the inferior, medial aspect of the proximal phalanx of the hallux
Applied Force:
Dorsiflexion and Inversion of the proximal phalanx of the hallux (relative to midline of the foot)
Flexor Hallucis Brevis 3rd Cuneiform Division
Client Position:
Supine
Plantarflexion of the foot
Plantarflexion of the proximal phalanx of the hallux
Tester Position:
Body: Stand to the side of involved foot
Stabilizing Hand: Brace 1st metatarsal
Action Hand: brace proximal phalanx of hallux
Applied Force:
Dorsiflexion of the proximal phalanx of the hallux
Adductor Hallucis Oblique Head
Client Position:
Supine, leg straight
Plantarflexion of the foot
Plantarflexion and adduction of the proximal phalanx of the hallux
Tester Position:
Body: Stand to the side of involved foot
Stabilizing Hand: Brace 1st met
Action Hand: brace proximal phalanx of the hallux
Applied Force:
Abduction of the proximal phalanx of hallux
Adductor Hallucis Transverse Head: Lateral Division
Client Position:
Supine, leg straight
Plantarflexion of the foot
Plantarflexion and inversion of the 4th, and 5th mets with plantarflexion at the 1st MTP-joint
Tester Position:
Body: Stand distal to body
Stabilizing Hand: brace the 1st met head
Action Hand: Brace dorsum of 4th and 5th metatarsal heads
Applied Force:
Dorsiflexion and eversion of the 4th and 5th metatarsals
Adductor Hallucis Transverse Head: Lateral Division
Client Position:
Supine, leg straight
Plantarflexion of the foot
Plantarflexion and inversion of the 4th, and 5th mets with plantarflexion at the 1st MTP-joint
Tester Position:
Body: Stand distal to body
Stabilizing Hand: brace the 1st met head
Action Hand: Brace dorsum of 4th and 5th metatarsal heads
Applied Force:
Dorsiflexion and eversion of the 4th and 5th metatarsals
Abductor Hallucis Longus Supinator Division
Client Position:
Supine, flex hip 45° and flex knee 90°
Plantarflexion of the foot
invert the forefoot on the rearfoot
Adduct the forefoot on the rearfoot Tester Position:
Body: Stand distal to body
Stabilizing Hand: Brace the calcaneus
Action Hand: medial aspect of hallux and 1st met
Applied Force:
Abduction of the forefoot on rearfoot through the hallux
Abductor Hallucis Longus Adductor Division
Client Position:
Supine, flex hip 45° and flex knee 90°
Plantarflexion of the foot
Adduct of the forefoot on the rearfoot
Tester Position:
Body: Stand distal to body
Stabilizing Hand: Brace the calcaneus
Action Hand: medial aspect of hallux and 1st met
Applied Force:
Abduction of the forefoot on rearfoot through the hallux
31. Micro Order 31, AMC&S Test
Flexor Digitorum Longus Lateral Division
Client Position:
Supine, leg straight
Plantarflexion with inversion of the foot
Plantarflex distal phalanges of lateral 2 toes (driving plantarflexion of the foot)
(point toes down and in)
Tester Position:
Body: Stand at side of involved foot
Stabilizing Hand: Brace middle phalanges
Action Hand: plantar surface of distal phalanges
Applied Force:
Dorsiflex distal phalanges of lateral 2 toes
Flexor Digitorum Longus Medial Division
Client Position:
Supine, leg straight
Plantarflexion with inversion of the foot
Plantarflex distal phalanges of medial 2 toes (driving ankle plantarflexion)
(point toes down and in)
Tester Position:
Body: Stand at side of involved foot
Stabilizing Hand: Brace middle phalanges
Action Hand: plantar surface of distal phalanges
Applied Force:
Dorsiflex distal phalanges of medial 2 toes
Flexor Digitorum BREVIS Lateral Division
Client Position:
Supine, leg straight
Plantarflexion with inversion of the foot
Plantarflexion of middle phalanx of lateral 2 toes.
Maintain extension of distal phalanx
Tester Position:
Body: Stand at side of involved foot
Stabilizing Hand: Brace proximal phalanx of lateral 2 toes
Action Hand: brace base of middle phalanges
Applied Force:
Dorsiflexion of the middle phalanx of the lateral 2 toes while maintaining extension of the distal phalanx
Flexor Digitorum BREVIS Medial Division
Client Position:
Supine, leg straight
Plantarflexion with inversion of the foot
Plantarflexion of the middle phalanx of medial 2 toes.
Maintain extension of distal phalanx
Tester Position:
Body: Stand at side of involved foot
Stabilizing Hand: Brace proximal phalanx of the medial 2 toes
Action Hand: brace base of middle phalanges
Applied Force:
Dorsiflexion of the middle phalanx of medial 2 toes while maintaining extension of the distal phalanx
Quadratus Plantae Lateral Head
Client Position:
Supine, leg straight
Plantarflexion with inversion of the foot
Plantarflex proximal phalanges of 4th and 5th toes while maintaining extension of middle and distal phalanx
Tester Position:
Body: Stand at side of involved foot
Stabilizing Hand: Brace metatarsal heads of lateral 2 toes
Action Hand: brace base of proximal phalanges of lateral 2 toes
Applied Force:
Dorsiflexion of the proximal phalanx of lateral 2 toes while maintaining extension of middle and distal phalanges
Quadratus Plantae Medial Head
Client Position:
Supine, leg straight
Plantarflexion with inversion of the foot
Plantarflexion of the proximal phalanges of 2nd and 3rd toes while maintaining extension of middle and distal phalanges
Tester Position:
Body: Stand at side of involved foot
Stabilizing Hand: Brace metatarsal heads of medial 2 toes
Action Hand: brace base of proximal phalanx of medial 2 toes
Applied Force:
Dorsiflexion of the proximal phalanx of medial 2 toes while maintaining extension of middle and distal phalanges
4th Plantar Lumbrical
Client Position:
Supine, leg straight
Plantarflexion with inversion of the foot*
Extension of the proximal phalanx of the 5th toe while maintaining extension of the middle and distal phalanges
Tester Position:
Body: Stand distal to body
Stabilizing Hand: Brace 5th metatarsal head
Action Hand: brace base of proximal phalanx of 5th metatarsal while maintaining middle and distal extension
Applied Force:
Dorsiflexion of the 5th toe
3rd Plantar Lumbrical
Client Position:
Supine, leg straight
Plantarflexion with inversion of the foot*
Extension of the proximal phalanx of the 4th toe while maintaining extension of the middle and distal phalanges
Tester Position:
Body: Stand distal to body
Stabilizing Hand: Brace 4th metatarsal head
Action Hand: brace base of proximal phalanx of 4th metatarsal while maintaining middle and distal extension
Applied Force:
Dorsiflexion of the 4th toe
2nd Plantar Lumbrical Client Position:
Supine, leg straight
Plantarflexion with inversion of the foot*
Extension of the proximal phalanx of the 3rd toe while maintaining extension of the middle and distal phalanges
Tester Position:
Body: Stand distal to body
Stabilizing Hand: Brace 3rd metatarsal head
Action Hand: brace base of proximal phalanx of 3rd metatarsal while maintaining middle and distal extension
Applied Force:
Dorsiflexion of the 3rd toe
1st Lumbrical
Client Position:
Supine, leg straight
Plantarflexion with inversion of the foot*
Extension of the proximal phalanx of the 2nd toe while maintaining extension of the middle and distal phalanges
Tester Position:
Body: Stand distal to body
Stabilizing Hand: Brace 2nd metatarsal head
Action Hand: brace base of proximal phalanx of 2nd metatarsal while maintaining middle and distal extension
Applied Force:
Dorsiflexion of the 2nd toe
3rd Plantar Interossei
Client Position:
Supine, leg straight
Plantarflexion with inversion of the foot
Plantarflexion of the proximal phalanx of the 5th toe
Tester Position:
Body: Stand distal to body
Stabilizing Hand: Brace 5th metatarsal
Action Hand: brace medial aspect of proximal phalanx of the 5th toe
Applied Force:
Dorsiflexion of the proximal phalanx of the 5th toe
2nd plantar interossei
Client Position:
Supine, leg straight
Plantarflexion with inversion of the foot
Plantarflexion of the proximal phalanx of the 4th toe
Tester Position:
Body: Stand distal to body
Stabilizing Hand: Brace 4th metatarsal
Action Hand: brace medial aspect of proximal phalanx of the 4th toe
Applied Force:
Dorsiflexion of the proximal phalanx of the 4th toe
1st Plantar Interossei
Client Position:
Supine, leg straight
Plantarflexion with inversion of the foot
Plantarflexion of the proximal phalanx of the 3rd toe
Tester Position:
Body: Stand distal to body
Stabilizing Hand: Brace 3rd metatarsal
Action Hand: brace medial aspect of proximal phalanx of the 3rd toe
Applied Force:
Dorsiflexion of the proximal phalanx of 3rd toe
Abductor Digiti Minimi
Client Position:
Supine, hip flexed 45 degrees with 90 degrees of knee flexion
Plantarflexion of the foot.
Abduction of the forefoot on rearfoot
Tester Position:
Body: Stand distal to body
Stabilizing Hand: Brace the calcaneus
Action Hand: Lateral and distal aspect of 5th metatarsal
Applied Force:
Adduction of the forefoot on the rearfoot
Flexor Digiti Minimi Brevis
Client Position:
Supine, leg straight
Plantarflexion of the foot
Flexion and abduction of the proximal phalanx of 5th toe
Keep distal phalanx extended
Tester Position:
Body: Stand distal to body
Stabilizing Hand: Brace the 5th metatarsal
Action Hand: brace base of 5th proximal phalange
Applied Force:
Dorsiflexion and adduction of the proximal phalanx of 5th toe
32. Micro Order 32, AMC&S Test
Longus Capitis
Tester Position:
Body: Stand distal to body
Stabilizing Hand: Brace hand on back of head
Action Hand: brace hand on front of head
Client Position:
Supine, tuck chin to flex head on neck
Rotate 20° toward uninvolved side
Fully flex cervical spine
Applied Force:
extend head on neck through plane of the head
Longus Colli: Superior Oblique Fibers
Tester Position:
Body: Stand distal to body
Stabilizing Hand: Brace hand on contralateral side of head
Action Hand: brace hand on ipsilateral side of head
Client Position:
Supine, fully rotate head to uninvolved side
Extend head on neck (Chin up)
Fully flex neck on trunk
Applied Force:
extend neck on trunk through sagittal plane
Longus Colli: Vertical Fibers
Tester Position:
Body: Stand distal to body
Stabilizing Hand: Brace hand on contralateral side of head
Action Hand: brace hand on ipsilateral side of head
Client Position:
Supine, fully rotate head to uninvolved side
Extend head on neck (Chin up)
Flex neck on trunk 25 degrees
Applied Force:
extend neck on trunk through sagittal plane
Longus Colli: Inferior Oblique Fibers
Tester Position:
Body: Stand distal to body
Stabilizing Hand: Brace hand on contralateral side of head
Action Hand: brace hand on ipsilateral side of head
Client Position:
Supine, fully rotate head to uninvolved side
Extend head on neck (Chin up)
Flex neck on trunk 5 degrees Applied Force:
extend neck on trunk through sagittal plane
Mylohyoid
Tester Position:
Body: Stand distal to body
Stabilizing Hand: Brace hand on back of head
Action Hand: brace hand on front of head
Client Position:
Supine, tuck chin to flex head on neck
Rotate 20° toward uninvolved side
Clench teeth with tongue to the roof of the mouth
Fully flex cervical spine
Applied Force:
extend head on neck through plane of the head
Sternohyoid
Tester Position:
Body: Stand distal to body
Stabilizing Hand: Brace hand on back of head
Action Hand: brace hand on front of head
Client Position:
Supine, Rotate head 20° toward uninvolved side
Extend head on neck (chin up)
Clench teeth with tongue to the roof of the mouth
Fully flex cervical spine
Applied Force:
Extend neck through plane of the head
Rectus Capitis Anterior
Tester Position:
Body: Stand distal to body
Stabilizing Hand: Brace on back of the head
Action Hand: brace anterior side of head
Client Position:
full flexion of head on neck and neck on trunk
Rotate head 45° to contralateral side
Applied Force:
Extend head on neck through oblique plane
33. Micro Order 33, AMC&S Test
Multifidus Cervicis Inferior Division
Tester Position:
Body: Stand distal to body
Stabilizing Hand: Brace hand around opposite ear
Action Hand: brace around involved ear
Client Position:
Full rotation of neck to opposite side
Lateral Flexion of neck to involved side
Tuck Chin
Applied Force:
Laterally flex neck though plane of table
Multifidus Cervicis Superior Division
Tester Position:
Body: Stand distal to body
Stabilizing Hand: Brace hand around opposite ear
Action Hand: brace around involved ear
Client Position:
Full rotation of neck to opposite side
Lateral Flexion of neck to involved side
Chin Up
Applied Force:
Laterally flex neck through plane of table
Sternocleidomastoid Sternal Fibers
Tester Position:
Body: Stand distal to body
Stabilizing Hand: Brace hand around opposite ear
Action Hand: brace palm of hand over temporal bone
Client Position:
Supine, Extend head on neck
Rotate 45° to contralateral side
Fully flex neck on trunk
Applied Force:
Extend neck on trunk in sagittal plane
Sternocleidomastoid Clavicular Fibers
Tester Position:
Body: Stand distal to body
Stabilizing Hand: Brace hand around opposite ear
Action Hand: brace around involved ear
Client Position:
Supine, Extend head on neck
Rotate 45° to contralateral side
Fully flex neck on trunk
Applied Force:
extend and sidebend neck on trunk though oblique plane
Longissimus Capitis
Tester Position:
Body: Stand on involved side of the body
Stabilizing Hand: Brace hand on contralateral side of head: use elbow to brace thoracic spine
Action Hand: Posterior side of head
Client Position:
Prone, full rotation to involved side
full extension of neck on trunk then head on neck
Applied Force:
Flex head on neck in sagittal plane (Separate mastoid from TP's)
Longissimus Cervicis
Tester Position:
Body: Stand on involved side of the body
Stabilizing Hand: Brace hand on contralateral side of head: use elbow to brace thoracic spine
Action Hand: Posterior side of head
Client Position:
Prone, full rotation to involved side
Full extension of neck on trunk
Flex head on neck
Applied Force:
flex neck on trunk through the sagittal plane (separate TP's)
Splenius Capitis
Tester Position:
Body: Stand on involved side of the body
Stabilizing Hand: Brace uninvolved side of head: use elbow to brace thoracic spine
Action Hand: posterior-lateral side of head
Client Position:
Prone, fully extend cervical spine
Fully rotate to involved side
Extend head on neck
Applied Force:
flex head through Sagittal plane
Splenius Cervicis
Tester Position:
Body: Stand on involved side of body
Stabilizing Hand: Brace uninvolved side of head: use elbow to brace thoracic spine
Action Hand: Posterior-lateral side of head
Client Position:
Prone, fully extend cervical spine
Fully rotate to involved side
Tuck chin
Applied Force:
flex head through sagittal plane
Iliocostalis Cervicis Tester Position:
Body: Stand on involved side of body
Stabilizing Hand: Brace uninvolved side of head: use elbow to brace thoracic spine
Action Hand: Lateral side of head
Client Position:
Prone, tuck chin
Rotate head to look over involved shoulder
Applied Force:
flex head through oblique plane
Rotatores Cervicis
Tester Position:
Body: Stand distal to body
Stabilizing Hand: Brace hand around opposite ear and skull
Action Hand: brace around involved skull
Client Position:
Full rotation of neck to opposite side
Lateral flexion to involved side
Chin up
Applied Force:
Counter-rotation of head and neck
Rectus Capitis Posterior Major
Tester Position:
Body: Stand distal to body
Stabilizing Hand: Brace hand around opposite side skull
Action Hand: brace around involved skull
Client Position:
Full flexion of neck on trunk
Extend head on neck
Rotate head 45° to ipsilateral side
Applied Force:
Rotate head to contralateral side
Obliques Capitis Inferior
Tester Position:
Body: Stand distal to body
Stabilizing Hand: Brace hand around opposite ear
Action Hand: brace around involved ear
Client Position:
full flexion of head on neck and neck on trunk (chin down)
Full rotation of head to ipsilateral side
Applied Force:
Rotate head to contralateral side
34. Micro Order 34, AMC&S Test
Semispinalis Capitis
Tester Position:
Body: Stand on involved side of body
Stabilizing Hand: anterior side of head: use elbow to stabilize thoracic spine
Action Hand: Brace hand on back of skull
Client Position:
Prone, rotate 20° to uninvolved side
Extend head
Fully extend cervical spine
Applied Force:
flex head and neck through plane of head
Semispinalis Cervicis
Tester Position:
Body: Stand on involved side of the body
Stabilizing Hand: anterior side of head: use elbow to stabilize thoracic spine
Action Hand: Brace hand on back of skull
Client Position:
Prone, rotate 20° to uninvolved side
Fully extend cervical spine
Flex head on neck
Applied Force:
Flex neck on trunk through plane of head
Spinalis Capitis
Tester Position:
Body: Stand on involved side of the body
Stabilizing Hand: Anterior side of skull
Action Hand: Brace hand behind ear on skull
Client Position:
Prone, slightly rotate to involved side
extend cervical spine 20°
extend head on neck
Applied Force:
flex head on trunk in sagittal plane in cocking motion
Spinalis Cervicis
Tester Position:
Body: Stand on side of body
Stabilizing Hand: Brace opposite shoulder
Action Hand: Brace hand behind ear on skull
Client Position:
Prone, slightly rotate to involved side
Flex head on neck
Extend cervical spine 20°
Applied Force:
flex head sagittal plane
Interspinalis Cervicis
Tester Position:
Body: Stand distal to body
Stabilizing Hand: Brace hand around front of head
Action Hand: posterior side of head on involved side
Client Position:
Extension of head and neck
Applied Force:
Cervical flexion
Obliques Capitis Superior
Tester Position:
Body: Stand distal to body
Stabilizing Hand: Brace hand around uninvolved side of skull
Action Hand: brace posterior skull on involved side
Client Position:
Full rotation of head to contralateral side
Flexion of neck on trunk
Flexion of head on neck
Applied Force:
extend head obliquely toward opposite ear
Rectus Capitis Posterior Minor
Tester Position:
Body: Stand distal to body
Stabilizing Hand: Brace hand around uninvolved side of skull
Action Hand: brace around involved side skull
Client Position:
Slight flexion of neck on trunk
Full extension of head on neck (chin up)
Slight rotation to involved side
Applied Force:
Flex head on neck
35. Micro Order 35, AMC&S Test
Posterior Scalenes AMC&S Test
Tester Position:
Body: Stand distal to body
Stabilizing Hand: Brace hand on uninvolved side of head above ear
Action Hand: brace hand on involved side of head above ear Client Position:
Supine, grab sides of table
rotate head 20° to uninvolved side
Slightly flex cervical spine
Flex and fully side bend neck on thorax through oblique plane
Chin up
Applied Force:
laterally flex and extend neck on thorax through oblique plane
Middle Scalenes
Tester Position:
Body: Stand distal to body
Stabilizing Hand: Brace hand on uninvolved side of head above ear
Action Hand: brace hand on involved side of head above ear
Client Position:
Supine, grab sides of table
rotate head 20° to uninvolved side
Slightly flex cervical spine
Flex and fully side bend neck on thorax through oblique plane
Chin up
Applied Force:
laterally flex neck on trunk through oblique plane with force coming from anterior to the ear
Anterior Scalenes
Tester Position:
Body: Stand distal to body
Stabilizing Hand: Brace hand around opposite side of head
Action Hand: brace hand on involved side of head
Client Position:
Supine, flex cervical spine 45°
rotate 20° away
Fully sidebend neck
extend head on neck (chin up)
Applied Force:
Laterally flex neck on trunk in oblique plane
Anterior Intertransversarii
Tester Position:
Body: Stand distal to body
Stabilizing Hand: Brace hand around opposite side of head
Action Hand: brace around involved side of head
Client Position:
Slight rotation of head to involved side
Lateral flexion of neck to same side
Tuck Chin
Applied Force:
Laterally flex neck coronal plane
Omohyoid
Tester Position:
Body: Stand distal to body
Stabilizing Hand: Brace hand around opposite side of head
Action Hand: brace around involved side of head
Client Position:
Full flexion of neck on trunk
20 degrees of rotation to opposite side
Capital extension
Shrug involved shoulder
Teeth clenched with tongue to roof of mouth
Applied Force:
Laterally flex and extend neck on trunk through oblique plane
Rectus Capitis Lateralis
Tester Position:
Body: Stand distal to body
Stabilizing Hand: Brace hand around uninvolved side of head
Action Hand: brace around involved side of head
Client Position:
Lateral flexion of head on neck
Applied Force:
Laterally flex head on neck through coronal plane
36. Micro Order 36, Muscle Test
Extensor Carpi Radialis Longus: Abductor Division
Client supine
Full Elbow flexion with forearm pronated*
Abduct/Radial Deviate hand at wrist and fully extend wrist emphasizing pressure through the 2nd met
Force:
Wrist Flexion with Adduction/Ulnar Deviation
(Force through 2nd met)
Extensor Carpi Radialis Longus: Extensor Division
Muscle Test
Client supine
Full Elbow flexion with forearm pronated*
Fully extend wrist emphasizing pressure through the 2nd met
FORCE: Wrist Flexion (Force through 2nd met)
Extensor Carpi Ulnaris: Adductor Division
Client supine
Full Elbow flexion with forearm pronated*
Adduct/Ulnar Deviate hand at wrist and fully extend wrist emphasizing pressure through the 5th met
FORCE: Wrist Flexion with Adduction/Ulnar Deviation
(force through 5th met)
Extensor Carpi Ulnaris: Extensor Division
Client supine
Full Elbow flexion with forearm pronated*
Fully extend wrist emphasizing pressure through the 5th met
FORCE: Wrist Flexion (Force through 5th met)
Extensor Carpi Radialis Brevis
Client supine
Full Elbow flexion with forearm pronated*
Fully extend wrist emphasizing pressure through the 3rd met
FORCE: Wrist Flexion with Adduction/Ulnar Deviation
(Force through 3rd met)
37. Micro Order 37, Muscle Test
Flexor Carpi Radialis: Abductor Division
Client supine
90° Elbow flexion with forearm supinated
Abduct/Radial Deviate and fully flex hand at wrist emphasizing pressure through 2nd met
FORCE: Wrist extension with adduction/ulnar deviation
(Force through 2nd met)
Flexor Carpi Radialis: Flexor Division
Client supine
90° Elbow flexion with forearm supinated
Fully flex hand at wrist emphasizing pressure through 2nd met
FORCE: Wrist extension (Force through 2nd met)
Flexor Carpi Ulnaris: Adductor Division
Client supine
90° Elbow flexion with forearm supinated
Adduct/Ulnar Deviate and fully flex hand at wrist emphasizing pressure through 5th met
FORCE: Wrist extension with adduction/ulnar deviation
(Force through 5th met)
Flexor Carpi Ulnaris: Flexor Division Client supine
90° Elbow flexion with forearm supinated
Fully flex hand at wrist emphasizing pressure through 5th met
FORCE: Wrist extension (Force through 5th met)
Palmaris Longus
Client supine
90° Elbow flexion with Supination and full wrist flexion
Point fingers and thumb together (eagles beak)
FORCE: Wrist extension
38. Micro Order 38, Muscle Test
Anconeus: Ulnar Division
Client supine
Fully extend elbow and supinate forearm
Force:
Pronate forearm, maintaining elbow extension
Anconeus: Olecranon Division
Client supine,
Flex elbow 45° and supinate forearm
Force:
Pronate forearm, with elbow flexed 45°
Supinator: Olecranon Division Muscle Test
Client supine
Supinate forearm with 90 degrees of elbow flexion
FORCE: Pronate forearm
Supinator: Ulnar Division
Client supine
Supinate forearm with full elbow flexion
FORCE: Pronate forearm
39. Micro Order 39, Muscle Test
Pronator Teres: Humeral Division
Client supine
Elbow extension with full pronation of forearm
FORCE: Supination of forearm
Pronator Teres: Ulnar Division
Client supine
Flex elbow 45° with full pronation of forearm
FORCE: Supination of forearm
Pronator Quadratus: Proximal Division
Client supine
Elbow flexed 90° with full pronation of the forearm (hand straight)
FORCE: Supination of forearm
Pronator Quadratus: Distal Division
Client supine
Full flexion of the elbow and full pronation of the forearm
FORCE: Supination of Forearm
40. Micro Order 40, Muscle Test
Extensor Pollicis Longus: Ulnar Division
Client supine
Elbow flexed 90 Degrees with forearm supinated
Extend distal phalanx of thumb with metacarpal abducted and radial deviation of the hand at the wrist
Brace proximal phalanx
FORCE: Flex distal phalanx on proximal phalanx
Extensor Pollicis Longus: Septal Division Muscle Test
Client supine
Elbow flexed 90 Degrees forearm pronated
Extend distal phalanx of thumb with metacarpal abducted and radial deviation of the hand at the wrist
Brace proximal phalanx
FORCE: Flex distal phalanx on proximal phalanx
Extensor Pollicis Brevis: Radial Division
Client supine
Elbow flexed 90 Degrees with forearm supinated
Extend and abduct proximal phalanx while flexing distal phalanx of thumb
Radial deviation of the hand at the wrist
Brace 1st metacarpal
FORCE: Flex and adduct proximal phalanx of the thumb
Extensor Pollicis Brevis: Septal Division
Client supine
Elbow flexed 90 Degrees with forearm pronated
Extend and abduct proximal phalanx while flexing distal phalanx of thumb
Radial deviation of the hand at the wrist
Brace 1st metacarpal
FORCE: Flex and adduct proximal phalanx of the thumb
Abductor Pollicis Longus: Radial Division
Client supine
Elbow flexed 90 degrees with forearm supinated
Abduct and extend 1st metacarpal (maintain flexion of distal phalanx)
Radial deviation of the hand at the wrist
Brace trapezium
FORCE: Flex and Adduct 1st metacarpal
Abductor Pollicis Longus: Ulnar Division
Client supine
Elbow flexed 90 degrees with forearm pronated
Abduct and extend 1st metacarpal (maintain flexion of distal phalanx)
Radial deviation of the hand at the wrist
Brace trapezium
FORCE: Flex and Adduct 1st metacarpal
41. Micro Order 41, Muscle Test
Flexor Pollicis Longus
Client supine
Elbow flexed 90 degrees with forearm supinated and wrist flexion
Flex distal phalanx on flexed proximal phalanx and adducted metacarpal
Brace proximal phalanx
FORCE: Extend distal phalanx on proximal phalanx
Abductor Pollicis Brevis
Client supine
Elbow flexed 90 Degrees with forearm supinated
Flex/abduct radial side of proximal phalanx of thumb forward and toward base of 5th met
Maintain extension of the distal phalanx
FORCE: extend/adduct proximal phalanx
Flexor Pollicis Brevis
Client supine
Elbow flexed 90 Degrees with forearm supinated
Flex proximal phalanx of thumb toward 5th met head
Maintain extension of the distal phalanx
FORCE: Extend proximal phalanx away from $5^{th}$
Adductor Pollicis Oblique Head
Client supine
Elbow flexed 90 Degrees with forearm supinated
Flex and Adduct ulnar side of thumb toward junction at the base of the 4th and 5th metacarpals
Maintain Extension of distal phalanx of the thumb.
FORCE: Extend proximal phalanx
Adductor Pollicis Transverse Head
Client supine
Elbow flexed 90 Degrees with forearm supinated
Flex and Adduct ulnar side of thumb toward 3rd metacarpal
Maintain extension of distal phalanx of thumb.
FORCE: Extend proximal phalanx
Interoseii Pollicis Client supine
Elbow flexed 90 degrees with forearm supinated
Flex and Adduct thumb toward 2nd metacarpal
Maintain extension of the distal phalanx of the thumb.
FORCE: Extend proximal phalanx
Opponens Pollicis Flexor Division
Client supine
Elbow flexed 90 degrees with forearm supinated
Flex and Abduct 1st metacarpal by touching tip of thumb to 5th finger
Extend the proximal phalanx of thumb.
FORCE: Extend 1st metacarpal
Opponens Pollicis Abductor Division
Client supine
Elbow flexed 90 degrees with forearm supinated.
Flex and Abduct 1st metacarpal by touching tip of thumb to 5th finger
Extend the proximal phalanx of thumb.
FORCE: Adduct 1st metacarpal
42. Micro Order 42, Muscle Test
Extensor Digitorum Medial Division
Client supine
Elbow flexed 90 degrees with forearm pronated and slight wrist flexion**
Extend 4th and 5th digits (1 at a time)
Maintain extension at inter-phalangeal joints
FORCE: Flex base of proximal phalanx of 4th and 5th digits
Grip fingers as a whole
Extensor Digitorum Lateral Division
Client supine
Elbow flexed 90 degrees with forearm supinated and wrist extended
Extend 2nd and 3rd digits (1 at a time)
Maintain extension at inter-phalangeal joints
FORCE: Flex base of proximal phalanx of 2nd and 3rd digits
Grip fingers as a whole
Extensor Indicis
Client supine
Elbow flexed 90 Degrees with forearm supinated
Extend and adduct 2nd digit
FORCE: Flex and abduct 2nd digit
Extensor Digiti Minimi
Client supine
Elbow flexed 90 degrees with forearm supinated
Extend and adduct the 5th digit
FORCE: Flex and abduct the proximal phalanx of the 5th digit through sagittal plane
4th Dorsal Interossei
Client supine
Elbow flexed 90 degrees with forearm supinated
Extend and abduct 4th digit toward 5th
FORCE: Adduct 4th digit toward $3^{rd}$
3rd Dorsal Interossei
Client supine
Elbow flexed 90 Degrees with forearm supinated
Extend and abduct 3rd digit toward 4th
FORCE: Adduct 3rd digit toward 2nd
2nd Dorsal Interossei
Client supine
Elbow flexed 90 Degrees with forearm supinated
Extend and abduct 3rd digit toward 2nd
FORCE: Adduct 3rd digit toward $4^{th}$
1st Dorsal Interossei
Client supine
Elbow flexed 90 degrees with forearm supinated
Extend and abduct 2nd digit toward 1st
FORCE: Adduct 2nd digit toward $3^{rd}$
43. Micro Order 43, Muscle Test
Flexor Digitorum Profundus Medial Division
Client supine
Elbow flexed 90 Degrees with forearm supinated and slight wrist extension**
Flex distal phalanx while extending proximal and distal phalanx of 4th and 5th digits
FORCE: Extend distal phalanx of 4th and 5th digits
Flexor Digitorum Profundus Lateral Division
Client supine
Elbow flexed 90 Degrees with forearm supinated and slight wrist extension
Flex distal phalanx while extending proximal and distal phalanx of 2nd and 3rd digits
FORCE: Extend distal phalanx of 2nd and 3rd digits
Flexor Digitorum Superficialis: Medial Division
Client supine
Elbow flexed 90 Degrees with forearm supinated and slight wrist extension**
Flex middle phalanx while extending distal phalanx of the 4th and 5th digits
FORCE: Extend middle and distal phalanx of 4th and 5th digits
Flexor Digitorum Superficialis: Lateral Division
Client supine
Elbow flexed 90 Degrees with forearm supinated and slight wrist extension
Flex middle phalanx while extending distal phalanx of the 2nd and 3rd digits
FORCE: Extend middle and distal phalanx of 2nd and 3rd digits
4th Lumbrical
Client Supine
Elbow flexed 90 Degrees with forearm supinated
Flex and adduct 5th digit
Brace base of proximal phalanx of 5th metacarpal while maintaining middle and distal extension
Force: Extension of the 5th digit
3rd Lumbrical
Client Supine
Elbow flexed 90 Degrees with forearm supinated
Flex 4th digit
Brace base of proximal phalanx of 4th metacarpal while maintaining middle and distal extension
Force: Extension of the 4th digit
2nd Lumbrical
Client Supine
Elbow flexed 90 Degrees with forearm supinated
Flex 3rd digit
Brace base of proximal phalanx of 3rd metacarpal while maintaining middle and distal extension
Force: Extension of the 3rd digit
1st Lumbrical
Client Supine
Elbow flexed 90 Degrees with forearm supinated
Flex 2nd digit
Brace base of proximal phalanx of 2nd metacarpal while maintaining middle and distal extension
Force: Extension of the 2nd digit
3rd Palmar Interossei
Client supine
Elbow flexed 90 Degrees with forearm supinated
Flex and adduct proximal phalanx of 5th digit toward 4th
FORCE: Extend and Abduct 5th digit away from $4^{th}$
2 nd Palmar Interossei Client supine
Elbow flexed 90 Degrees with forearm supinated
Flex and adduct proximal phalanx of 4th digit toward 3rd
FORCE: Extend and Abduct 4th digit away from 3rd
1st Palmar Interossei
Client supine
Elbow flexed 90 Degrees with forearm supinated
Flex and adduct proximal phalanx of 2nd digit toward 3rd
FORCE: Extend and Abduct 2nd digit away from $3^{rd}$
Flexor Digiti Minimi
Client supine
Elbow flexed 90 Degrees with forearm supinated
Flex proximal phalanx of the 5th digit
FORCE: Extend proximal phalanx of 5th digit
Abductor Digiti Minimi Flexor Division
Client supine
Elbow flexed 90 Degrees with forearm supinated
Flex and abduct the proximal phalanx of 5th digit
FORCE: Extend proximal phalanx of 5th digit
Abductor Digiti Minimi Abductor Division
Client supine
Elbow flexed 90 Degrees with forearm supinated
Flex and abduct proximal phalanx of 5th digit down and away from ulna
FORCE: Extend and adduct proximal phalanx of 5th digit
Oponens Digiti Minimi Manus Flexor Division
Client supine
Elbow flexed 90 Degrees with forearm supinated
Flex and abduct 5th metacarpal
FORCE: Extend 5th metacarpal
Oponens Digiti Minimi Manus Abductor Division
Client supine
Elbow flexed 90 Degrees with forearm supinated
Flex and abduct 5th metacarpal
FORCE: Extend and adduct 5th metacarpal
Palmaris Brevis
Client supine
Elbow flexed 90 Degrees with forearm supinated
Flex and adduct 5th metacarpal to Approximate toward 1st metacarpal
FORCE: Separate 5th metacarpal from 1st Systems and Kits Embodiments provided herein also include systems and kits for facilitating and enhancing the maintenance of a subject's muscle set-points.

Kits in accordance with the present disclosure include exercise instructions and corresponding exercise equipment for properly stressing (exercise) a subject's muscle using the same basic macro and micro hierarchy shown above. Kits may include an instruction sheet and figures showing the exercise order for maximum benefit for any one muscle pattern or for any two or more patterns, up to instructions for all 43 movement patterns. Optionally, appropriate exercise equipment for specific stress to a primary or secondary muscle is provided in a kit. Exercise equipment in some aspects is designed to support ACM&S.

Systems in accordance with the present disclosure include kits and memory/computing devices for keeping track and personalizing a subject's muscle contractile profile at any one time. For example, a computer that stores and updates a subject's treatment and/or exercise status based on the embodiments herein. The memory/computing device could track muscle set points (primary and secondary) based on a health care professional's input. Objective criteria could be used for input based on the health care professional assessment and overall treatment or exercise regimes developed based on a subject's status.

The following examples are provided for illustrative purposes only and are not intended to limit the scope of the invention.

What is claimed is:

1. A method for identifying, activating, and treating a target muscle within a muscle group having a weakness, the method comprising:
    identifying the muscle group having the weakness by testing the muscle group using a first Active Muscle Contract and Sustain Test (AMC&S), including challenging a plurality of testing positions in a pattern according to Example 2;
    subsequent to identifying the muscle group having the weakness, activating the muscle group with a process comprising:
        applying a first Muscle Specific Applied Stress (MSAS) to a first muscle in the identified muscle group, the first muscle having a highest priority in an established hierarchy of muscles within the muscle group, the established hierarchy of muscles being shown in Table 1;
        subsequent to the applying the first MSAS, applying a two-step activation process to the first muscle in the identified muscle group and moving to each muscle in priority of the muscle group according to the established hierarchy of muscles within the muscle group, the two-step activation process comprising:
            first, applying a second AMC&S challenging testing positions in the pattern according to Example 2; and
            second, activating the muscle group using an activation technique;
    subsequent to activating the muscle group with the two-step activation process, treating the muscle group in an activated state with a treatment comprising:
        applying a second MSAS to treat each muscle in priority until reaching a priority of the target muscle; and
        subsequent to applying the second MSAS, applying a third MSAS to treat each muscle in priority until reaching the priority of the target muscle,
    wherein the treatment to the target muscle in the activated state results in an increase in a set point of the target muscle as compared to a similarly treated muscle which is not in the activated state.

2. The method of claim 1, wherein the increase in the target muscle's set point results in an increase in the target muscle's contractile efficiency as compared to the target muscle's contractile efficiency prior to the increase in set point.

3. The method of claim 1, wherein the treatment results in an increase in the target muscle's overall muscle efficiency comprising enhancing the overall muscle efficiency by activating the target muscle in a macro-pattern hierarchy.

4. The method of claim 3, further comprising activating the target muscle in a micro-pattern hierarchy within each macro-pattern.

5. A method for identifying, activating, and treating a target muscle within a muscle group having a weakness on each side of a patient, the method comprising:
    identifying the muscle group having the weakness by testing the muscle group using a first Active Muscle Contract and Sustain Test (AMC&S), the testing including:
        challenging a plurality of testing positions in movement patterns accordinc to Example 2 within which the target muscle is on a left side of the patient; and following the challenging on the left side of the patient, challenging the plurality of testing positions in movement patterns according to Example 2 within which the target muscle is on a right side of the patient;

subsequent to identifying the muscle group having the weakness, activating the muscle group with the weakness, the activating the muscle group with the weakness comprising:

applying a first Muscle Specific Applied Stress (MSAS) on a primary muscle for an identified movement pattern on the left side of the patient; and following the applying on the left side of the patient, applying the first MSAS on a primary muscle for an identified movement pattern on the right side of the patient;

subsequent to the applying the first MSAS, applying a two-step activation process to the primary muscle in the identified muscle group on the left side of the patient and moving to each muscle in priority of the muscle group on the left side of the patient according to an established hierarchy of muscles within the muscle group, the two-step activation process comprising:

first, applying a second AMC&S on the left side of the patient challenging testing positions in a pattern according to Example 2; and second, activating the muscle group using an activation technique on the left side of the patient; and subsequent to activating the muscle group with the two-step activation process on the left side of the patient, applying the two-step activation process to the primary muscle in the identified muscle group on the right side of the patient and moving to each muscle in priority of the muscle group on the right side of the patient according to the established hierarchy of muscles within the muscle group, the two-step activation process comprising:

first, applying the second AMC&S on the right side of the patient challenging testing positions in the pattern according to Example 2; and second, activating the muscle group using the activation technique on the right side of the patient; and subsequent to activating the muscle group with the two-step activation process, treating the muscle group in an activated state with a treatment comprising:

applying a second MSAS to the left side of the patient to treat each muscle in priority until reaching the priority of the target muscle; and subsequent to applying the second MSAS to the left side of the patient, applying the second MSAS to the right side of the patient to treat each muscle in priority until reaching the priority of the target muscle; and subsequent to applying the second MSAS on the right side of the patient, applying a third MSAS to treat each muscle on the left side of the patient in priority until reaching the priority of the target muscle; and subsequent to applying the third MSAS to the left side of the patient, applying the third MSAS to treat each muscle on the right side of the patient in priority until reaching the priority of the target muscle, wherein the treatment to the target muscle in the activated state results in an increase in a set point of the target muscle as compared to a similarly treated muscle which is not in the activated state.

6. The method of claim 1, wherein the treatment to each muscle in an identified movement pattern results in each muscle in the identified movement pattern having an improved ability to tolerate force following the treatment.

7. The method of claim 1, wherein the muscle group having the weakness is treated in a bilateral ordered fashion in the first MSAS from pattern 1 through pattern 43.

8. The method of claim 7 where each pattern has both primary and secondary muscles.

9. The method of claim 8 wherein a primary muscle of pattern 1 through pattern 43 is shown in Table 1.

10. The method of claim 9 wherein the secondary muscles of pattern 1 through pattern 43 are shown in Table 2.

11. The method of claim 1, wherein the activation technique is administering a Digital Force Application To Muscle Attachment Technique (DFAMAT) according to a DFAMAT pattern shown in Table 3.

12. The method of claim 1, wherein the activation technique is administering a Positional Isoangular Contraction (PIC) technique according to a pattern shown in Table 3.

13. The method of claim 5, wherein the primary muscle is a first muscle having a highest priority in the established hierarchy of muscles within the muscle group, the established hierarchy of muscles being shown in Table 1.

* * * * *